US011887731B1

(12) United States Patent
Gallagher et al.

(10) Patent No.: US 11,887,731 B1
(45) Date of Patent: Jan. 30, 2024

(54) SYSTEMS AND METHODS FOR EXTRACTING PATIENT DIAGNOSTICS FROM DISPARATE

(71) Applicant: Select Rehabilitation, Inc., Glenview, IL (US)

(72) Inventors: Michael Gallagher, Chicago, IL (US); Michael Capstick, Chicago, IL (US); Matthew Moran, Chicago, IL (US)

(73) Assignee: SELECT REHABILITATION, INC., Glenview, IL (US)

( * ) Notice: Subject to any disclaimer, the term of this patent is extended or adjusted under 35 U.S.C. 154(b) by 754 days.

(21) Appl. No.: 16/855,682

(22) Filed: Apr. 22, 2020

Related U.S. Application Data

(60) Provisional application No. 62/837,023, filed on Apr. 22, 2019.

(51) Int. Cl.
| | |
|---|---|
| G06F 40/20 | (2020.01) |
| G16H 50/20 | (2018.01) |
| G16H 10/60 | (2018.01) |
| G16H 10/20 | (2018.01) |
| G16H 10/40 | (2018.01) |
| G16H 70/20 | (2018.01) |

(Continued)

(52) U.S. Cl.
CPC ............. *G16H 50/20* (2018.01); *G06F 40/30* (2020.01); *G06N 3/045* (2023.01); *G06N 3/047* (2023.01); *G06N 3/08* (2013.01); *G06V 30/18* (2022.01); *G06V 30/413* (2022.01); *G16H 10/20* (2018.01); *G16H 10/40* (2018.01); *G16H 10/60* (2018.01); *G16H 70/20* (2018.01)

(58) Field of Classification Search
CPC ...................................................... G06F 40/20
See application file for complete search history.

(56) References Cited

U.S. PATENT DOCUMENTS

| | | | | |
|---|---|---|---|---|
| 5,148,287 A | * | 9/1992 | Kemmochi | ........ H04N 1/40037 358/3.03 |
| 5,539,840 A | * | 7/1996 | Krtolica | ............... G06V 10/751 382/204 |

(Continued)

OTHER PUBLICATIONS

Neumann ("ScispaCy: Fast and Robust Models for Biomedical Natural Language Processing"), Feb, (Year: 2019).*

*Primary Examiner* — Jae U Jeon
(74) *Attorney, Agent, or Firm* — Baker, Donelson, Bearman, Caldwell & Berkowitz, P.C.

(57) ABSTRACT

A method is described herein that comprises receiving scanned documents, wherein the scanned documents comprise unstructured data. The method includes performing optical character recognition of the scanned documents to produce text data for each page of the scanned documents, wherein the text data for each page comprises a sequence of words stored together with their location. The method includes dividing each page of the scanned documents into subsections. The method includes using the text data to identify a structure type of each subsection of a page, wherein the structure type includes at least one of a table and text paragraph. The method includes using the text data to label each subsection of a page with a semantic type, wherein the semantic type defines a context surrounding collection of information in a subsection. The method includes using the text data for each subsection of a page to identify medical concepts.

19 Claims, 18 Drawing Sheets

(51) Int. Cl.
  *G06N 3/08* (2023.01)
  *G06F 40/30* (2020.01)
  *G06V 30/413* (2022.01)
  *G06N 3/045* (2023.01)
  *G06N 3/047* (2023.01)
  *G06V 30/18* (2022.01)

(56) References Cited

U.S. PATENT DOCUMENTS

| | | | | |
|---|---|---|---|---|
| 5,995,204 A | * | 11/1999 | Hoshino | H04N 1/00273 |
| | | | | 358/487 |
| 6,332,036 B1 | * | 12/2001 | Sakamoto | H04N 1/56 |
| | | | | 382/165 |
| 6,947,176 B1 | * | 9/2005 | Kubo | H04N 1/6027 |
| | | | | 358/1.9 |
| 10,909,985 B1 | * | 2/2021 | Whittenburg | H04L 63/166 |
| 2004/0143594 A1 | * | 7/2004 | Kalies | G16H 15/00 |
| 2010/0303360 A1 | * | 12/2010 | Matsuda | H04N 1/3871 |
| | | | | 382/195 |
| 2016/0012038 A1 | * | 1/2016 | Edwards | G06F 40/30 |
| | | | | 704/9 |
| 2016/0148079 A1 | * | 5/2016 | Shen | G06N 3/0454 |
| | | | | 382/157 |
| 2016/0314104 A1 | * | 10/2016 | Phillips | G06F 40/151 |
| 2018/0068083 A1 | * | 3/2018 | Cohen | G16H 50/20 |
| 2018/0317840 A1 | * | 11/2018 | Ben-Kiki | A61M 21/02 |
| 2019/0166211 A1 | * | 5/2019 | Price | H04L 43/0817 |
| 2019/0286978 A1 | * | 9/2019 | Aggarwal | G06N 20/00 |
| 2020/0159232 A1 | * | 5/2020 | Refaat | G06N 5/04 |

* cited by examiner

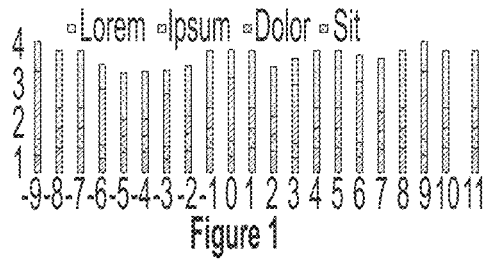
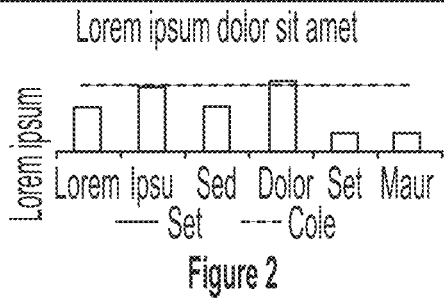
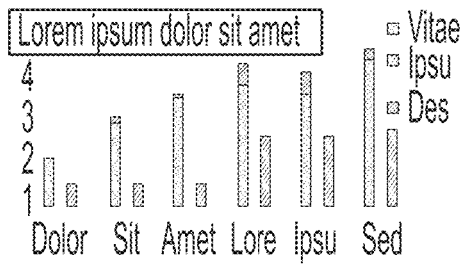
FIG. 2D

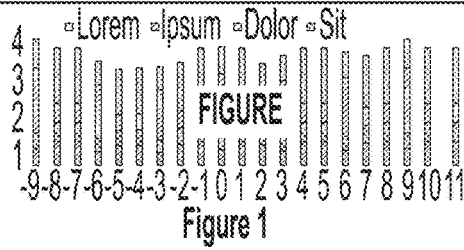
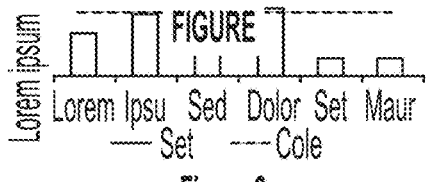
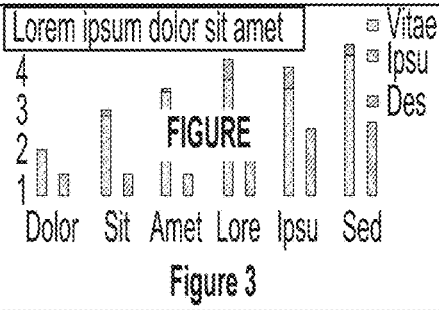
FIG. 2E

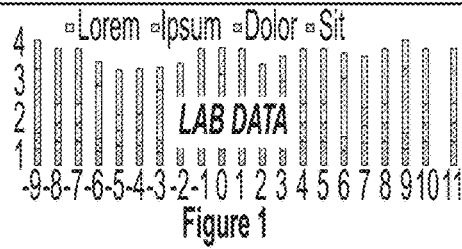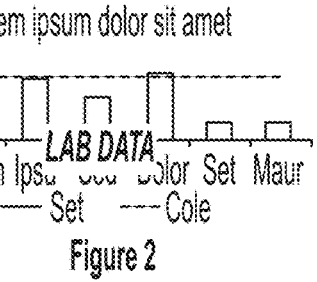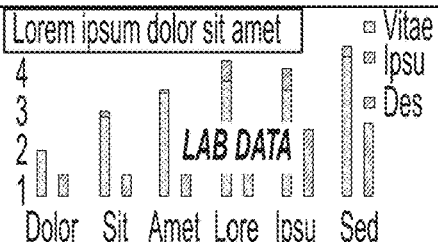
FIG. 2F

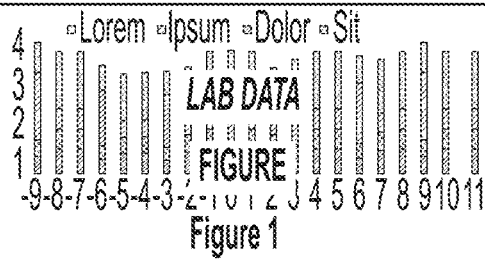
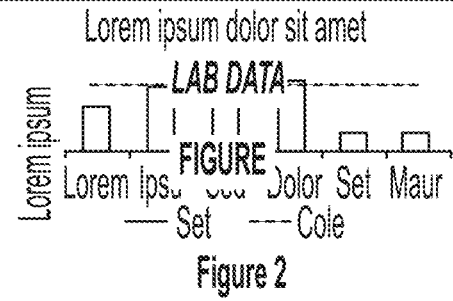
FIG. 2G

FIG. 5

M0300 B1. Unhealed Stage 2 Pressure Ulcers — 500

A Stage 2 Pressure Ulcer is a partial thickness loss of dermis presenting as a shallow open ulcer with a red-pink wound bed, without slough or brusing. it may also present as an intact or open/ruptured blister. — 510

Were any of the resident's unhealed pressure ulcers Stage 2?

Make a selection
- ◉ Yes.
- ○ No.

How many were there?

Enter a number: 3

— 520

Resources — 530
- Item Rationale
- Steps for Assessment
- Coding Instructions and Tips
- Examples Save and continue Signed in as:

Sunrise Care Center
Switch: Facility

John Doe
Switch: Patient

Nov. 7, 2018 MDS Case
↑ Load Documentation

MDS Builder
- ◉ Section GG
- ◉ Section H
- ◉ Section I
- ◉ Section J
- ◉ Section K
- ... Section M — 550
- Section N — 552
- Section O ⊕ Previous MDS Case
⊕ New MDS Case

MDS Case Review and Export

Select Solutions™ provides automated reccomendations for MDS Items based on information found in facility EMRs as well as uploaded documents. In some cases, if accurate, a single recommendation might increase the estimated Medicare reimbursement. In other cases, a combination of accepted recommendations may have a significant impact on reimbursement.

These 3 recommendations have been identified as an instance of significant reimbursement impact if all 3 are accepted:

| Status | MDS Item | | Recommended Value(s) | Current Value(s) |
|---|---|---|---|---|
| Declined | 10020B | Primary Diagnosis | G93.41 Metabolic Encephalopathy | J12.9 Pneumonia |
| Declined | 18000 | Additional Diagnoses | J12.9 Pneumonia<br>169.991 Dysphagia | None |
| Declined | K0510 C. | Mechanically Altered Diet | Yes | No |

Facility Name
Switch Facility

John Doe
Switch Patient

Nov. 7, 2018 MDS Case
Load Documentation
MDS Builder

FIG. 9A

Please review these recommendations for accuracy. Click each MDS Item to see the details of the recommendation and Accept if appropriate. If all 3 recommendations are accepted the estimated reimbursement and case-mix indices/groups will change in this manner.

Before accepting the above 3 recommendations:

| Rate Component | Case-Mix Group | Case-Mix Index | Reimbursement |
|---|---|---|---|
| Nursing | CBC1 | 1.34 | $138.63 |
| NTA (days 1-3) | NF | 0.72 | $168.60 |
| PT | TK | 1.52 | $90.18 |
| OT | TK | 1.54 | $85.05 |
| SLP | SA | 0.68 | $15.04 |

AFTER accepting the above 3 recommendations:

| Rate Component | Case-Mix Group | Case-Mix Index | Reimbursement |
|---|---|---|---|
| Nursing | HBC2 | 2.23 (+0.89) | $230.72 (+$92.09) |
| NTA (days 1-3) | NB | 2.53 (+1.81) | $592.41 (+$423.81) |
| PT | TO | 1.55 (+0.03) | $91.96 (+$1.78) |
| OT | TO | 1.55 (+0.01) | $85.61 (+$0.56) |
| SLP | SE | 2.33 (+1.65) | $51.61 (+$36.57) |

The total estimated daily reimbursement by accepting the 3 recommendations would be:

First 3 days of the stay: $1,052.31 (+$554.81) per day
4th day through discharge: $657.37 (+$272.81) per day Click the button below to generate and download a partially completed MDS pdf file.

[Export PDF]

Previous MDS Case
⊕ New MDS Case

FIG. 9B

SYSTEMS AND METHODS FOR EXTRACTING PATIENT DIAGNOSTICS FROM DISPARATE

RELATED APPLICATIONS

This application claims the benefit of U.S. Application No. 62/837,023, filed Apr. 22, 2019.

TECHNICAL FIELD

The disclosure herein involves systems and methods for collecting and providing health care data.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE DRAWINGS

FIG. 2D shows a document analysis component, under an embodiment.

FIG. 2E shows a document analysis component, under an embodiment.

FIG. 2F shows a document analysis component, under an embodiment.

FIG. 2G shows a document analysis component, under an embodiment.

FIG. 5 shows an electronic data management user interface, under one embodiment.

FIG. 9A shows an electronic data management user interface, under one embodiment.

FIG. 9B shows an electronic data management user interface, under one embodiment

DETAILED DESCRIPTION

Figure 1:
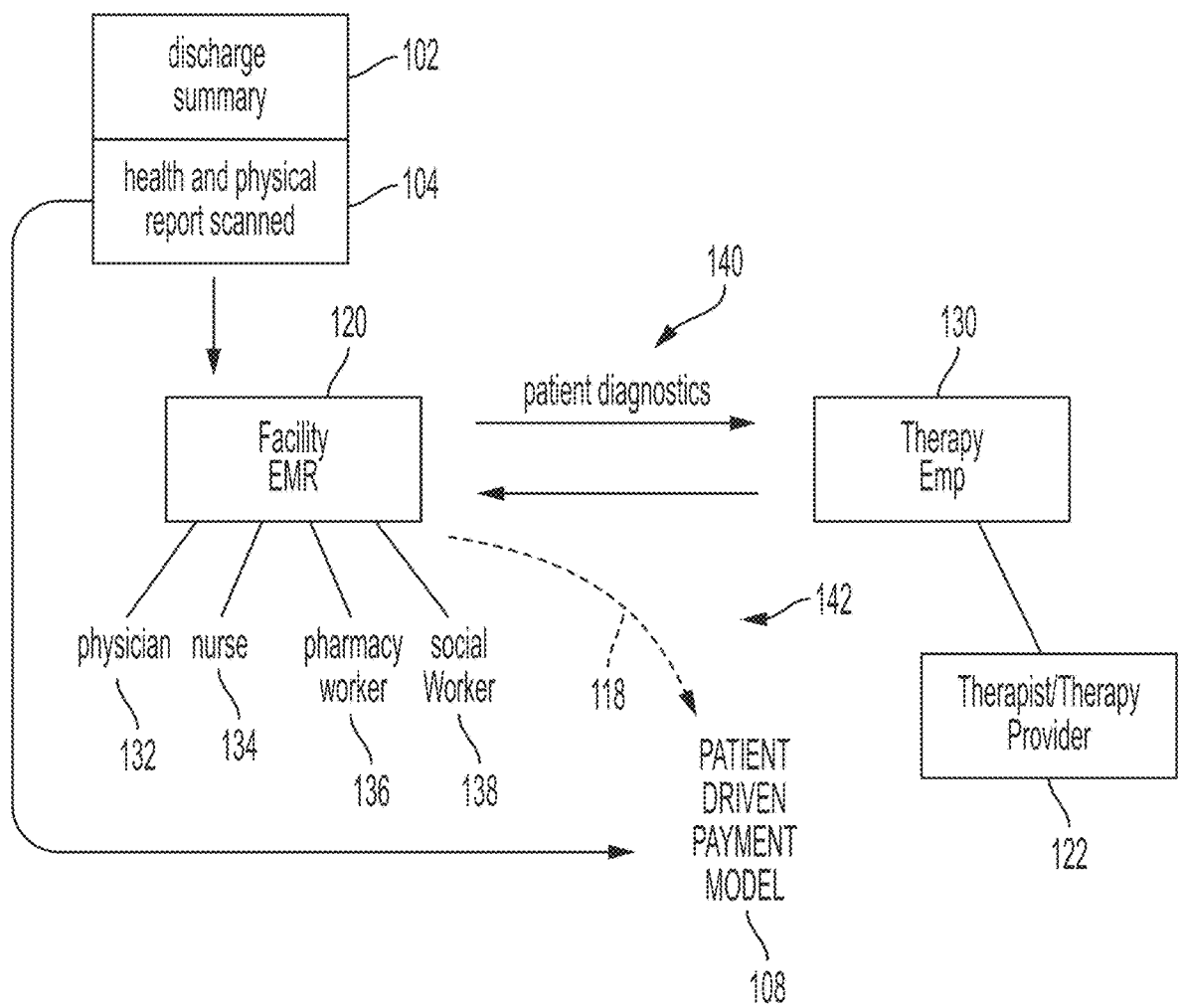
FIG. 1 shows flow of data among systems receiving and managing data of a skilled nursing facility, under an embodiment.

Consistent documentation and ICD*10 coding that accurately reflects the condition, treatment needs, and goals of the patient is a fundamental requirement in today's health care environment. This can be challenging, as documentation is often split across multiple Electronic Health Record systems that do not interface. When patients transfer from one health care setting to another, the patients' medical records also transfer from the referring facility (acute care hospital) to the new facility (a skilled nursing facility (SNF)). The records are often sent via a .pdf file or faxed. These records are then either scanned and saved in the SNF electronic medical record or placed in a physical chart. Timely and accurately reviewing of the acute hospital records is time consuming and challenging for the SNF and may result in inaccurate or incomplete coding of various reports, documentation systems, assessments and billing claims.

Within the same health care facility, multiple EMR systems exist as well. For instance, in a skilled nursing facility, two separate disciplines, nursing and speech therapy, may assess the patient's cognitive functions and record this information in two separate and unrelated EMR systems. The information recorded may be similar or very different as patient's interaction for cognitive function may differ based on the time of day, environment, hydration level, medication intake of the patient etc. In a perfect world, during a care plan meeting, the nurse and the speech language pathologist (SLP) would discuss their individual findings and then code the documentation based on which situation most accurately represents the individual patient. Utilizing separate systems may lead to the inaccurate and inefficient delivery of health care and coding of services provided to the patient.

The fragmentation of documentation, and the lack of integration within our existing health care records needs to be addressed. The Office of the National Coordinator for Health Information Technology (ONC) has identified six barriers to healthcare interoperability:

1. Technical barriers. These limit interoperability through—for example—a lack of standards development, data quality, and patient and healthcare provider data matching.
2. Financial barriers. These relate to the costs of developing, implementing and optimizing health IT to meet frequently changing requirements of healthcare programs, including lack of incentives for sharing information and need for business models for secondary uses of data.
3. Trust barriers. Legal and business incentives to keep data from moving present challenges. Health information networks and their participants often treat individuals' electronic health information as an asset that can be restricted to obtain or maintain competitive advantage.
4. Administrative requirements. Federal documentation and administrative requirements (including billing requirements) contribute to health IT burden due to outdated guidelines for evaluation and management codes that unnecessarily link payment to documentation.
5. Reporting requirements. Federal reporting requirements in some cases add burden to healthcare providers by requiring them to report on quality measures that are not relevant or meaningful.
6. IT usability. "Health IT system design and usability barriers identified by stakeholders include . . . variations in the design [of user-interfaces] that make day-to-day use complicated when a healthcare provider uses multiple systems and the lack of developer engagement with end users of health IT regarding design needs."

A tool is described herein that facilitates under an embodiment efficient interdepartmental communication and enhances the accuracy of completing the Minimum Data Set (MDS), which is the mandated process of clinical assessment for all patients in Medicare and Medicaid certified nursing homes. The tool is referred to herein as a Patient Driven Payment Model (PDPM). The PDPM may be referred to herein as the system, the PDPM system, the tool, or the PDPM tool. The system extracts actionable details from hospital discharge documentation, therapy documentation, nursing notes and other sources of information. The system's data mining and expert system capabilities support the SNF in deciding on the most accurate and consistent coding of the medical record. The tool identifies details from the documentation that are relevant to the coding decisions faced by the SNF. The knowledge base of the expert system consists of rules and patterns that assist the user in resolving conflicting documentation and link those choices to specific supporting material in the patient record.

System Overview

FIG. 1 shows the flow of data at a skilled nursing facility (SNF) 100. The facility may receive unstructured data from multiple sources including discharge summaries 102 and/or health and physical reports 104. These summaries and/or reports arise under one embodiment when a patient is discharged from emergency facilities and transported to a SNF 100. These data sources 102,104 generally exist in paper form and are scanned into an electronic format. The scanned data is under one embodiment provided to a patient driven payment model (PDPM) 108 as described herein. Under an alternative embodiment, the scanned data is provide to the SNF 100 and then electronically sourced 118 to the PDPM.

Data managed by the SNF may comprise facility EMR data 120 and therapy EMR data 130. Note that a SNF may employ or cooperate/interact with multiple health care professionals including physicians 132, nurses 134, pharmacy workers 136, and social workers 138. In treating and caring for SNF patients, these health care providers generate and provide patient health care data to a facility Electronic Medical Record (EMR) database. A SNF may also employ or work collaboratively with therapy providers 122. In rehabilitating and caring for SNF patients, therapy personnel 122 (e.g. physical therapists, speech therapists, etc.) provide data to a therapy Electronic Medical Record (EMR) database 130. The facility EMR and the therapy EMR may exchange patient diagnostic date 140 under an embodiment. The PDPM may then use a combination of facility EMR data, therapy EMR data, and unstructured data to recommend MDS.

Figure 2A:
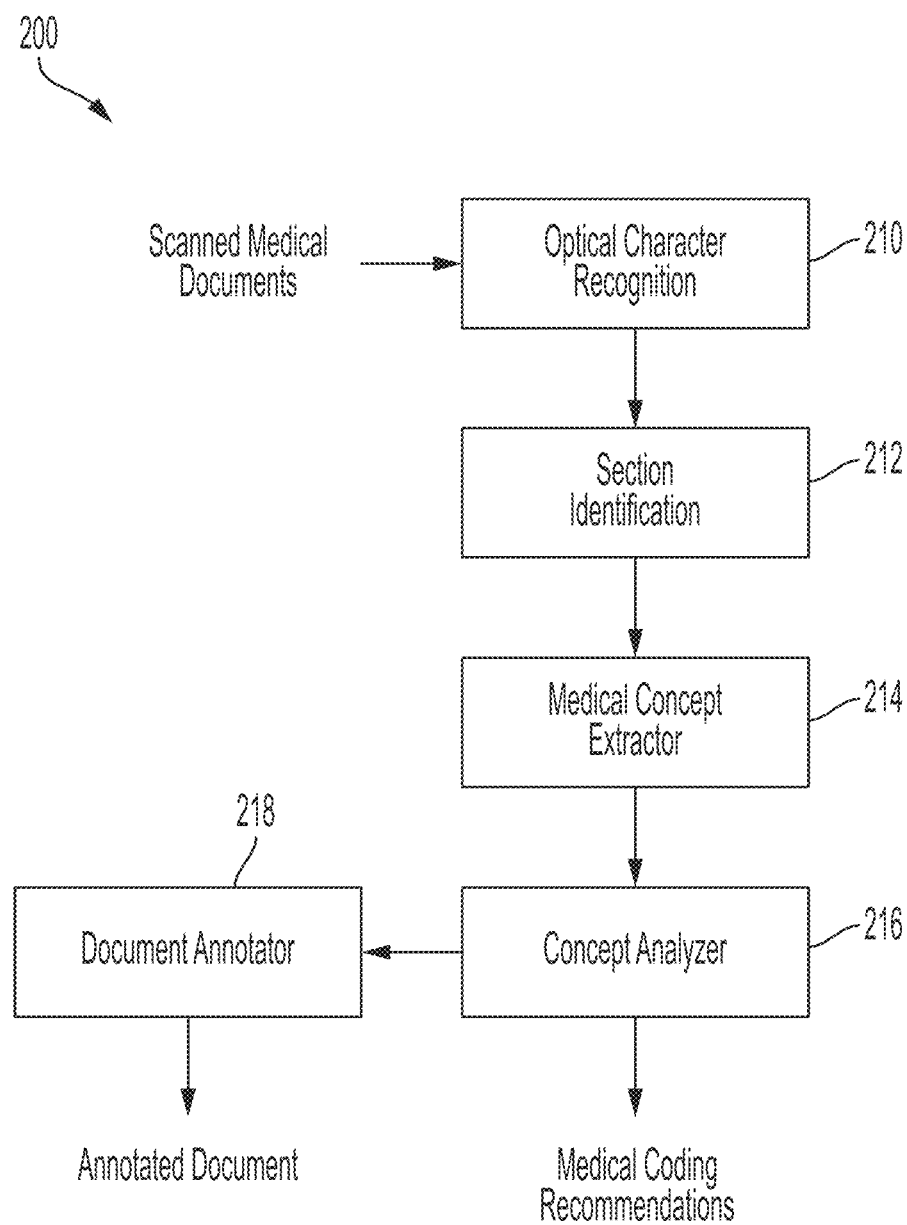
FIG. 2A shows components of an electronic document analysis and data management system, under an embodiment.

The system (FIGS. 2A and 2B) consists of components in three distinct areas: components for collecting and analyzing the patent record, a user interface for the MDS Coordinator to interact with the system, and a learning component for the system to learn from the choices of the users. Note that the individual at an SNF responsible for entering MDS codes for incoming and resident patients comprises the user or MDS user of the system described herein.

The Document Analyzer 200 and Case Analyzer 220 subsystems are focused on understanding the patient file to draw observations on the patient's condition. The Document Analyzer processes individual documents that may have come from external care providers, like a hospital. The documents could be scanned paper documents or documents sourced electronically (e.g., the health and physical report and/or discharge summary). Where the Document Analyzer processes a single document, the Case Analyzer reviews the analysis results from all the documents in the patient's case and from any EMR data delivered through the EMR Gateway 240 (as further described below). The Case Analyzer 220 merges the analysis results from all the data sources and makes the consolidated analysis available to the User Interface 290 (as further described below).

The User Interface 290 is responsible for providing a view into the analysis for the user and walking the user through all the steps necessary to determine the appropriate coding for the patient.

The Knowledge Learning System 230 monitors all the analysis results, in each component, and the users decisions to help the system designers identify new patterns and relationships between the various data elements and the choices being made by the user. The knowledge learned is fed back to the system to improve its ability to analyze the input data and provide observations and considerations to the user.

Document Analyzer

The Document Analyzer 200 sub-system processes unstructured documentation, like PDF documents or document scans. The subsystem consists of five (5) components (FIG. 2A): Optical Character Recognition (OCR) 210, Section Identification 212, Medical Concept Extractor (MCE) 214, Concept Analyzer 216, and Document Annotator 218.

Optical Character Recognition

The OCR component 210 converts document images into a text stream that can be processed by the other components in the Document Analyzer. Raw output of OCR comprises a sequence of words or partial words stored together with their location (x, y coordinates and page number) and size in the original image.

Section Identification Component

Clustering may be used to determine sections of text, under an embodiment. A section may be a paragraph, a table, a list, header or footer. The clustering algorithm used is Hierarchical Density-Based Spatial Clustering of Applications with Noise (HDBSCAN) with a distance measure tuned to identifying blocks of text in scanned pages, under an embodiment. The distance measure calculates the amount of whitespace between different words and skips over the space attributed to the actual words. In this way the HDBSCAN algorithm focuses on identifying clusters where the whitespace increases in size significantly.

The sections output from the clustering are broken into lines using the position and size information of each word in the section, under an embodiment.

The sections identified above may or may not have headings. The sections identified above could also be a single line that is a heading. It depends on the structure of the original document. Once the sections are identified the system processes section headings and subject related groups of sections. For example, if a section has a heading "Past Medical History" and the subsequent 2 sections are purely text describing the patients past medical conditions, and neither section has a heading of its own, then the system will join the 3 sections into a single section with the topic label "Past Medical History".

Headings are identified by looking at the first line of a section, under an embodiment. The first line may be considered a heading if it begins on the left of the section, and has two or more of: larger font than the remaining lines, ends in a colon, is exclusively in upper case or each individual word is capitalized.

Each section is then categorized as to type of section. A section may be regular prose, table, list, etc. The sectioning code comprises a generic list of section types (e.g. past medical history, assessment, plan of care, medications, lab results etc). Correct identification of the section type allows the system to make determinations about the value and relevance of information extracted from the section.

Section type identification is achieved by matching the section text against the characterization of the uniqueness of words, and word combinations, for each type of section. The word usage characterization of the different section types is achieved by analyzing a corpus of examples for each section type. A word usage model is built by analyzing the frequencies of different types of words contained in the training set. Specifically, frequencies are calculated for single words of length greater than 4 characters, 2 word phrases, 3 word phrases, 4 word phrases and words where all characters are upper case. These frequencies can then be compared against sample blocks of text and the closest match determines the type of section for the sample block of text. Several techniques are possible for performing the match. One such embodiment is to total the frequencies of matched words and word combinations in the section type frequency sets and divide the result by the size of the text block. The larger the result the more confident the system can be of the classification.

Section Identification 212 (as described above) splits the document into its constituent sections and captures meta data about each section. All documents consist of text organized into sections, often delineated by headings and subheadings. Each section conveys information about the context of the section content. For example: "Past Medical History" informs the system that the contents of the section should refer to health conditions that the patient has had for an extended period of time or had in the past. The nature and purpose of a particular section is utilized downstream from the Section Identification component to draw conclusions on the meaning and relevance of information from the section.

Under an alternative embodiment, the Section Identification component may identify the structure of the section (e.g. lists, paragraphs or tables) using a Page Blocker component 282, a Section Structure Classifier component 284, and a Text Classifier component 286. All three components work together to divide each page of the document into sections and to identify the purpose of each section (past medical history, current medical history, laboratory results, medications, etc).

FIGS. 2C-2G demonstrate how an original document 280 (comprising medical information) passes through the various sub-components and is partitioned into sections and the sections classified. The original document comprises unstructured data. The Page Blocker 282 (shown in FIG. 2D) operates on the page to produce an initial division of the page into sections of text. As seen in FIG. 2E, the Section Structure Classifier 284 reviews each section identified by Page Blocker to determine the type of section: paragraph, list, table or cell in a table. The Text Classifier 286 (shown in FIG. 2F) labels a section with its type (e.g. past medical history, current medical history, laboratory results, medications, etc). The tool combines information from the Section Structure Classifier and the Text Classifier into a final product (FIG. 2G, 288).

Page Blocker

The Page Blocker manages the process of dividing a page into smaller sections where each section has a homogenous semantic type (e.g. table of medications, paragraphs of present medical condition, paragraphs of past medical history, tables of medical test results, etc). The process of dividing a page (or sub-section of a page) is further described below. Page Blocker achieves its goal by splitting the page into smaller sections based on areas of white space and testing its splits with the sub-components: Section Structure Classifier and Text Classifier. The Section Structure Classifier will tell Page Blocker if the section under review is a table, multi-column or a composite section.

The Section Structure Classifier provides a confidence that a section is a table. The Page Blocker will use this confidence, combined with the semantic unity considerations, to understand if splitting a section, suspected of being a table, raises or lowers the probability of the section containing a table. If making a sub-division means that one of the sub-sections produces a higher table confidence then Page Blocker knows that the sub-division is further isolating the table from other non-table sections and the sub-division should be kept. Alternatively, if the sub-division produces a lower confidence from the Section Structure Classifier then Page Blocker knows the sub-division is splitting apart the table and the sub-division should not be kept, the original whole section is a table. The other component used by Page Blocker, in the assessment of the quality of a sub-division, is the semantic unity of the resulting sub-sections. The semantic unity needs to improve in both pieces and the table confidence, from the Section Structure Classifier, of at least one of the pieces must improve OR both pieces are not strongly table-like. The semantic unity is calculated using the Gini Impurity. In this context, Gini Impurity is used to measure how well the given classification matches the purpose of the section text. Each line, in the section text, is classified and the resulting classification counts are used in the Gini Impurity calculation, as the probabilities for each class. For example: if a section of text had 4 lines and 3 classified as "past medical history' and one classified as "medications" then the calculation would be performed with the probability for "past medical history" as 3/4 and the probability for "medications" as 1/4.

If Section Structure Classifier determines that the section under review is not a likely to be a table, Page Blocker will use a different approach. Page Blocker will split the section along the most significant white space breaks and test each sub-section in turn as already described above with respect to the Page Blocker/Section Structure Classifier examination of table. Further decomposing the sub-sections where appropriate. Page Blocker also uses Text Classifier to determine if 2 adjacent sub-sections are of the same type. If the sub-sections are of the same type then Page Blocker will not leave the two sections separate in the final decomposition of the document.

Page Blocker identifies areas of white space that could be good points for sub-dividing the section by calculating pixel densities. The Page Blocker creates 2 vectors of the pixel density in the vertical and horizontal directions by summing the foreground color along the column and row. By reviewing each directional vector for points where the value falls near to zero the location of columns and rows of whitespace can be identified. These columns and rows of whitespace are the points in the page where section breaks can be made.

A further enhancement is to calculate the pixel density vectors using the pixel spans based on OCR word boundaries rather than simply each row and column of pixels. The OCR process identifies the pixel positions of the word boundaries as well as the actual words. Different characters have different pixel densities and those density differences lessen the effectiveness of the pixel density vectors, for example which portion of the letter 't' is cut by a density vector will affect the contribution of the letter to the density value. The vector passing through the stick of the 't' will have more density than a neighboring vector passing through one of the branches of the 't'. Ideally, wherever the vector cut the letter the result would be the same. By using the word boundaries from the OCR process to block the entire word as a rectangle, the relative densities of different letters and words is eliminated. The entire word will have the same value where ever the vector cuts the word. This approach results in a much clearer identification of the runs of white space.

FIG. 2D shows a division of a page into sections, under an embodiment.

Section Structure Classifier

The Section Structure Classifier reviews each section identified by Page Blocker to determine the type of section: paragraph, list, table or cell in a table. If the section is determined to be part of a table the section will be recombined with other sections that are part of the table. In that way the Section Structure Classifier ensures that tables are not split into disconnected pieces.

The Section Structure Classifier is a machine learning model that determines the type of block (paragraph, list, table). The model uses the whitespace between rows and columns of text to identify the structure of the document. The Section Structure Classifier takes in an image of the section of document under consideration, applies a multi-stage neural network which produces a vector of probabilities. The output probabilities predict whether the section of document is a table, structured as multi-column page or is some other construct (e.g. paragraphs). The Section Structure Classifier can be utilized to classify an entire page or a sub-section of a page. As such it can be used in an iterative manner to decompose a page into sub-sections with different structural elements. For example a page with paragraphs of text and tables could be split into sections for each table and paragraph. Page Blocker working with Section Structure Classifier is designed to perform that exact decomposition of the page.

FIG. 2E shows section types identified by Section Structure Classifier including text block, table, and figure, under and embodiment.

Figure 2B:
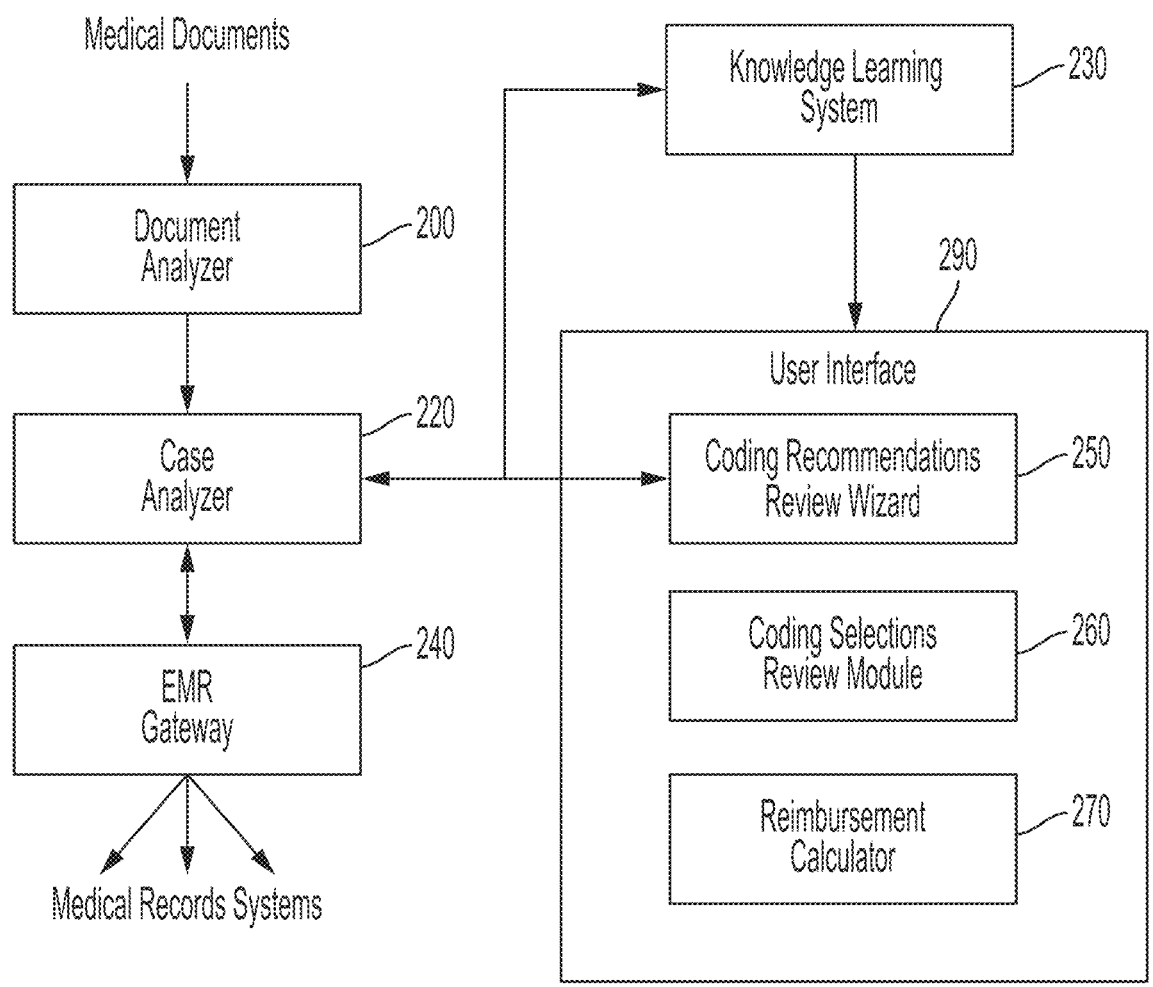
FIG. 2B shows components of an electronic document analysis and data management system, under an embodiment.
Figure 2C:
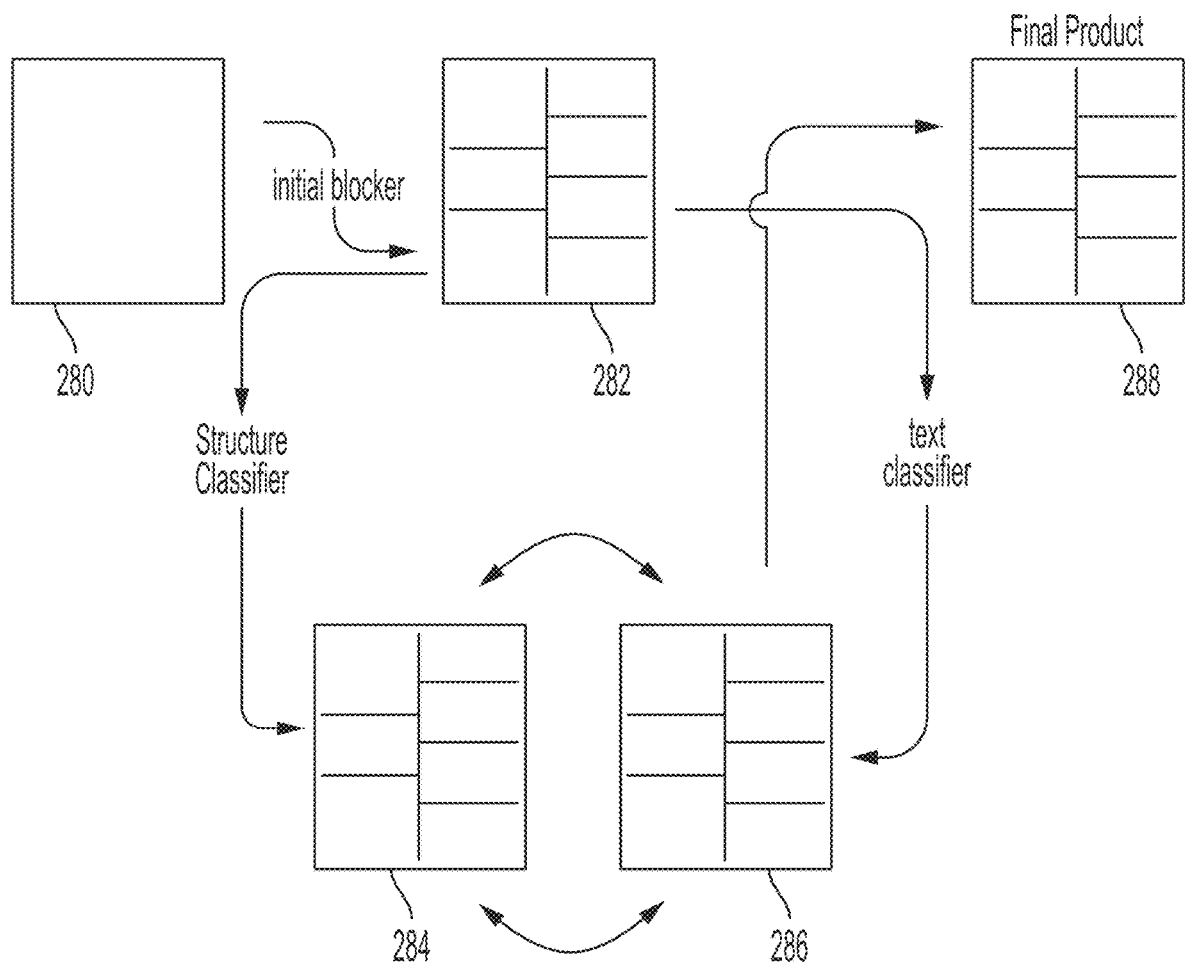
FIG. 2C shows components of an document analysis system, under an embodiment.
Figure 2H:
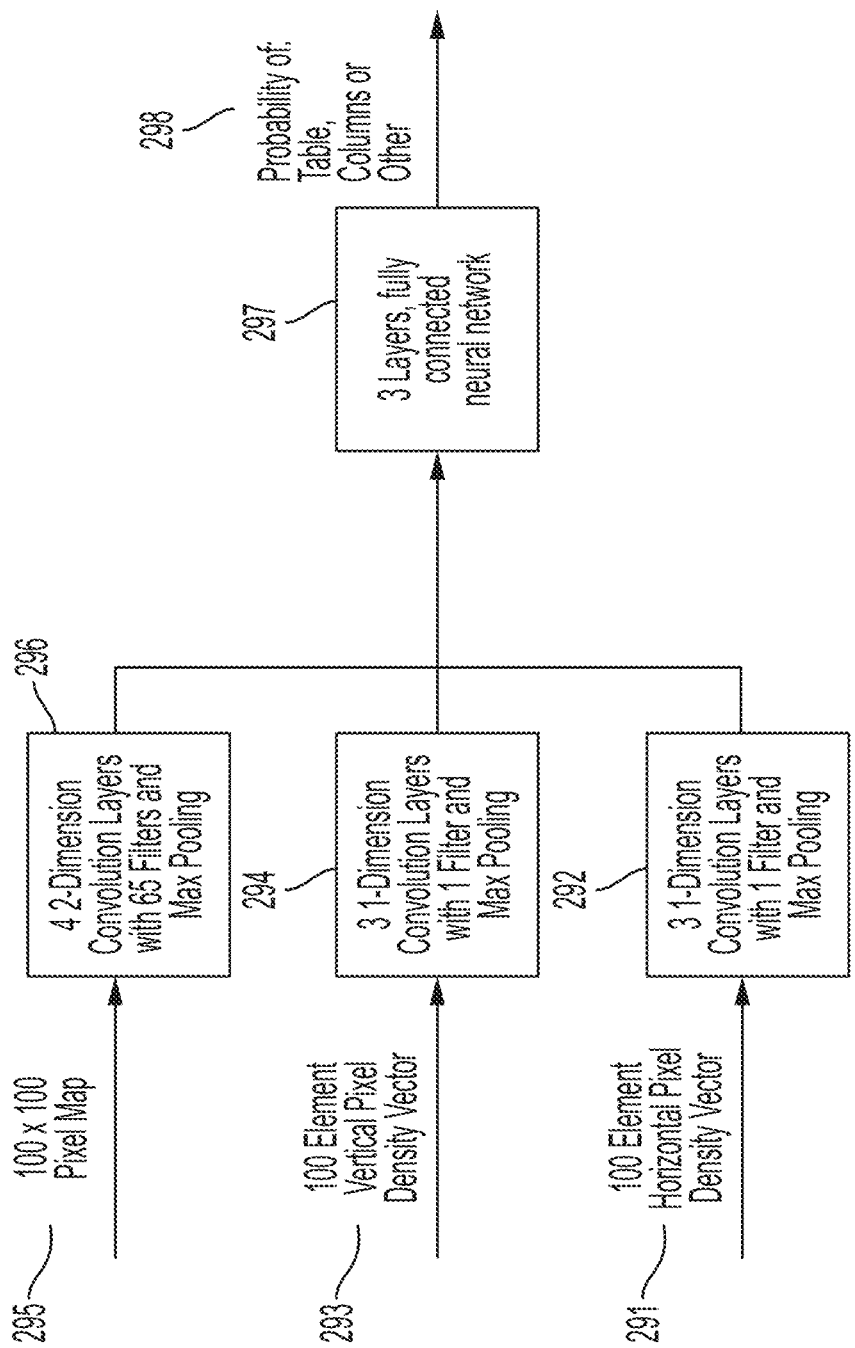
FIG. 2H shows a neural network, under an embodiment.

The Section Structure Classifier is constructed from a multi-stage deep learning neural network as shown in FIG. 2H. The input is a matrix of the pixel values of the section of page under consideration and the pixel density vectors from the Page Blocker. The 100 element horizontal pixel density vector 290 is fed into an independent neural network 291 comprising 3 one dimensional convolutional layers with a single filter and max pooling. The 100 element vertical pixel density vector 293 is fed into an independent neural network 294 comprising 3 one dimensional convolutional layers with a single filter and max pooling. The matrix of pixel values, for the section of document under consideration, is the same 100×100 matrix down-scaled in the Page Blocker. The 100×100 matrix of pixel values 295 is feed into its own neural network 296. The neural network 296 consists of 4 2-dimension convolutional layers with 65 filters and max pooling. The results of the 3 neural networks are combined and feed into a fourth fully connected 3 layer neural network 297 for classification. The output 298 of the classification neural network is a 3 valued vector. The 3 values represent the networks confidence that the section of document under consideration is a table, or a multi-column section, or something that is neither a multi-column section or a table (e.g. paragraphs). Note that the 100 element horizontal and vertical pixel density vectors are obtained by summing across the 100×100 matrix of pixel values in the horizontal and vertical directions, respectively.

FIG. 2E shows section types identified by Section Structure Classifier including text block, table, and figure. Although FIG. 2E shows figures, it should be noted that the Section Structure Classifier interprets figures as an absence of text. The OCR process extracts the characters only from the document, it joins the characters into words. And tells us what the word is, i.e. the x,y coordinates of the word location and the dimensions of the box that encloses the words. So if a page has a figure there won't be anything in the OCR but rather just a space with no words. So if the section is not a table and not a multi-column then it must a block of text (paragraph or group of paragraphs).

Text Classifier

The Text Classifier labels a section with its type (e.g. past medical history, current medical history, laboratory results, medications, etc). The Text Classifier works with Section Structure Classifier and Page Blocker, during sectioning, to ensure that the results of splitting blocks of text genuinely result in two new sections with different types.

The Text Classifier is a machine learning model that takes in sequences of text and returns the type of section (diagnosis/assessment/plan, medications, physical exam, lab results, radiology results, therapy notes, nursing notes, patient information, hospital boilerplate, patient education, etc.) indicated by the text. The sequence of text being classified is encoded using a GloVe (Global Vectors for Word Representation) word embedding model and passed to a classification model consisting of: two Long Short Term Memory (LSTM) layers which feeds a neural network stage consisting of 3 fully connected layers. The output of the classification model is the networks best effort at identifying the type of text sequence under consideration.

GloVe is an unsupervised learning algorithm for obtaining vector representations for words. Training is performed on aggregated global word-word co-occurrence statistics from a corpus. The GloVe word embedding model is trained on samples of text from hospital documentation. The text, from the documents, is preprocessed to tokenize keywords like ICD10 Codes, common first names, common last names, times of day, dates, URLs, drug names and different type numerical values. The tokenization helps the word embedding learn the type of text more efficiently without over fitting to specific values. The Text Classifier has been trained on a corpus of labelled sections from hospital documentation, like Discharge Documents, Patient Health and Physical Documents, nursing notes, laboratory results, etc. Under an embodiment, this documentation is grouped according to the categories comprising output of the Text Classifier.

The functioning of each component may occur multiple times as the document is decomposed into smaller sections. This produces text sections which include Section Type (semantic content), Section Structure (paragraph, list, table), Section Classification (past medical history, current medical history, laboratory results, medications, etc.), Section Text (words and their ordering), and Text Metadata (coordinates of text).

Section 2F shows the output of text classifier, under an embodiment.

Medical Concept Extractor

Medical Concept Extractor 214 (MCE) searches the text stream of each section for phrases, word patterns and concepts that are relevant to the medical domain. Each identification is recorded with meta data detailing the location, concept and sense of the concept. As indicated above each section is recorded with Section Type (semantic content), Section Structure (paragraph, list, table), Section Text (words and their ordering), Section Classification (past medical history, current medical history, laboratory results, medications, etc.), and Text Metadata (coordinates of text). The MCE is implemented using natural language processing techniques, text search techniques, and an expert system with knowledge of medical concepts relevant to the long-term care domain.

The core of the Medical Concept Extractor is a language model trained on clinical, scientific and biomedical text. The language parser is used to parse blocks of text into sentences and create a dependency graph of the sentence structure, including part of speech tagging (noun, verbs, subjects, objects, etc). A second function of the language parser is a Named Entity Recognition (NER) component that has been trained to distinguish anatomical entities, drugs/medications, diseases/disorders and signs/symptoms. The Medical Concept Extractor, uses both components of the language model, to identify phrases and entities within sentences and produce sentence dependency graphs of the phrases and entities. Sentence dependency graphs are used to collect modifiers for each entity so that tagging based on laterality, negation, identified disease stage (e.g. Stage 3 lung cancer), etc. can be tied back to the correct entities.

The language model (i.e. the dependency graphing and entity recognition) is built from the open source ScispaCy model which is a Python package containing spaCy models for processing biomedical, scientific or clinical text. The ScispaCy model has been trained on biomedical documents. The model then implements dependency graphing and entity recognition on new documents. The Named Entity Recognition aspects of the ScispaCy model was customized using transfer learning, to better suit the system's needs. Labelled entities from hospital documentation like discharge documents, history and physical documents and nursing notes were used to refine the ScispaCy language model training. The transfer learning enhanced the ScispaCy language models ability to recognize and identify medical concepts of interest to this system including: anatomical entities, drugs/medications, diseases/disorders and signs/symptoms.

Examples of the upgraded Named Entity Recognition capabilities are:

Given the input "Medication List: Fluticasone 27.5—1 spray both nostrils once a day" the NER will identify the following phrase/entity combinations [("Fluticasone", "DRUG/MEDICATION"), ("nostrils", "ANATOMICAL ENTITY")]. Other sections of the system (i.e., Concept Analyzer) use this output to make determinations on recommendations for the user. In this example the system sees that the patient is currently receiving the drug Fluticasone which is a common treatment for Asthma or COPD. The system may use this knowledge to confirm a diagnosis of COPD or Asthma, or the system may ask the user if the patient has either disease given the administration of the drug.

Or if the input is "Septic Shock—improved, off pressors, due to UTI and L Foot wound. Noted swelling of the L ankle" the NER produces the following phrase/entity combinations [("Septic Shock", "DISEASE/DISORDER"), ("pressors", "DRUG/MEDICATION"), ("UTF", "DISEASE/DISORDER"), ("L Foot wound", "DISEASE/DISORDER"), ("swelling", "SIGN/SYMPTOM"), ("L ankle", "ANATOMICAL ENTITY")]

The output of the NER, for this example, provided the system with information to help identify several possible ICD10 codes: S91.302D (Unspecified open wound, left foot, subsequent encounter), R22.42 (Localized swelling, mass and lump, left lower limb), R65.21 (Severe sepsis with septic shock), N390 (Urinary tract infection, site not specified) and the possible need to select M01040A Infection of the foot on the MDS form.

An example of the functioning of the language model: "Diabetes without complications." This sentence gets parsed into two entities, "diabetes" and "complications". The dependency parser links the object ("diabetes") to the modifier ("complications"). Since the preposition implies a negation, the system will identify that there are NOT complications for the diabetes. This observation will drive the choice of ICD10 code in subsequent layers of the software.

An another example of the functioning of the language model, laterality is used to indicate the side or position of a diagnosis. For example "left leg" would have "left" flagged as laterality so that the coding is able to reason about which leg is involved. One of the big changes from ICD9 to ICD10 is the increased level of specificity required. It is necessary to know that the leg has a break and which leg.

As indicated above, the Medical Concept Extractor (MCE) 214 searches text streams of each section identified by Section Identification 212 for phrase, word patterns, and concepts that are relevant to the medical domain. Each section identification is recorded with meta data. The approach identifies relevant phrases, word patterns, and concepts using a medical ontology. An ontology represents a set of concepts and categories in a subject area or domain. The ontology in use by the PDPM (the MCE ontology) comprises concepts and categories in the medical domain directed to long term care. As one example, the MCE may identify pneumonia as a term appearing in the underlying data processed by OCR 210 and Section Identification 212. The MCE uses the MCE ontology to identify terms and concepts related to pneumonia such as the term/concept of "disease" and a list of various pneumonia disease types.

Medical Concept Extractor understands the structure of text section and will adjust its approach in certain cases. Lists and tables require special approaches to ensure the output of the language model is interpreted in the right context.

Lists often have fragmented language, missing punctuation and inconsistent line breaks. Medical Concept Extractor applies custom rules for sentence splitting to retain sentences that span multiple lines in a list with fragmented language and missing punctuation. The rules cover address leading character capitalization, bulleted list and numerical list markers and line changes to break lists into appropriate fragments to assist the language model to produce valid results.

Sections that have been identified as tabular are fed to a Table Parser. The Table Parser traces alignment of text pieces to identify rows and columns. The structure of the table is managed by constructing a graph based on proximity and alignment of the text pieces. It forms lines that are horizontally aligned into rows and looks for columns where text is vertically aligned. Once the table structure is identified the Medical Concept Extractor can apply the language model cell by cell, in that way ensuring that the output of the model is not corrupted by running two unrelated pieces of text together.

Concept Analyzer

The Concept Analyzer's role is to take the concepts identified by the MCE and translate into entries for the Minimum Data Set (MDS), either MDS field entries or ICD10 codes. The Concept Analyzer may map an individual MCE entity (i.e., an entity identified by the MCE as described above) to an MDS item, or to an ICD10 code or may combine multiple MCE entities to determine an ICD10 code and could also deduce the necessity for further codes derived from existing codes, e.g. the need for after surgical care because the patient recently had surgery. The Concept Analyzer is the key component in analyzing the knowledge found in a single document and deciding how to map that knowledge to the MDS.

The Concept Analyzer 216 is constructed from a Document Model and an expert system. The Document Model contains knowledge on the various types of medical documentation processable by the system. It also contains specifics about how to compare information between the sections of the various documents. For example: chronic illnesses identified in document sections covering past medical conditions can be considered to still be active with the patient. Under one embodiment, the Concept Analyzer may identify chronic asthma in a past medical condition section. This means that this condition is actionable, i.e. the Concept Analyzer should proceed in mapping this condition forward to MDS coding. However, underlying documentation may refer to a past surgical procedures such as a hip replacement surgery performed three years ago. The occurrence of a past hip replacement surgery has no relevance to current MDS coding of the patient. Therefore, the Concept Analyzer does not act upon this information, i.e. does not map this information forward to corresponding MDS sections.

The Concept Analyzers' expert system consists of scenarios and rules for drawing actionable conclusions from the output of the MCE. The expert system has rules from translating the MCE output to coding actions in the MDS. It also has rules and scenarios for enhancing the MCE output through the addition of further concepts, ICD10 codes and MDS coding recommendations. For example, the presence of a concept indicating the patient had surgery during the hospital stay will trigger the Concept Analyzer to add concepts for post-surgery care and corresponding ICD 10 coding. The Concept Analyzer may then proceed with MDS mapping. As another example, underlying documentation may identify pneumonia in an Impression section. (Note that an Impression section represents a clinical summation of information and may be identified by the Section Identification component described above). This information is important due to the fact that the Impression section includes current diagnosis information. However, a Medication Section (identified by the Section Identification Component above) may indicate treatment of the pneumonia with antibiotics. Therefore, the Concept Analyzer is able to identify the condition as bacterial pneumonia.

The identification of ICD 10 codes is the primary method for describing the full set of a patients diagnoses. One algorithm the Concept Analyzer uses to generate ICD 10 codes from the MCE output is to look for MCE entities that directly identify ICD 10 codes. For example, the Concept Analyzer may use the term pneumonia to identify the ICD 10 codes related to pneumonia. This operation may use information of a phrase/entity combination identified by the MCE, under an embodiment. Under another embodiment, the relevant ICD 10 codes may directly appear in the underlying documentation. The ICD 10 codes may then be used to identify corresponding sections of the MDS. ICD10 code identification and selection is further described below.

If the code is specified directly the hospital documentation, it has a 95% confidence (the last 5% is to allow for an OCR error).

If the code is drawn from phrases in the documentation then the system determines a confidence measure based on the number of matches to clinically significant words in the description, as a percentage. For example:

If the search text is "bilateral carotid artery stenosis" the following scores would be recorded for the code options: (The identification of search text may use information of a phrase/entity combination identified by the MCE, under an embodiment).

80%→Occlusion and stenosis of bilateral carotid arteries (I65.23)
0%→Occlusion and stenosis of right carotid artery (I65.21)
0%→Occlusion and stenosis of left carotid artery (I65.22)
0%→Occlusion and stenosis of unspecified carotid artery (I65.29)
Resulting in a selection of I65.23

If the search text is "carotid artery stenosis" the following scores would be recorded for the same code options:

60%→Occlusion and stenosis of bilateral carotid arteries (I65.23)
60%→Occlusion and stenosis of right carotid artery (I65.21)
60%→Occlusion and stenosis of left carotid artery (I65.22)
75%→Occlusion and stenosis of unspecified carotid artery (I65.29)
Resulting in a selection of I65.29

Plurals are normalized to the singular version of the word ("arteries" becomes "artery"). Abbreviations are replaced with the full term and the term "unspecified" is ignored. A significant word from the search string missed in the ICD10 description will result in a non-match, hence the 0% when "bilateral" is not matched.

Where a family of codes have an equal match with the search phrase all the codes will be returned to the user sorted by frequency of choice as learned by the Knowledge Learning System.

Additional examples of Case Analyzer functionality follow:

From "Sepsis—like due to UTI" the MCE identifies disease entities: "Sepsis" and "UTI. The Concept Analyzer will map "Sepsis" to the ICD10 code "A41.9 (Sepsis, unspecified organism)" and make it available for consideration for MDS item I0020B. The MDS item I2100 will also be recommended as needing to be checked. The entity "UTI" is mapped, by the Concept Analyzer, to the ICD10 code "N39.0 (Urinary tract infection, site not specified)" and make it available for consideration for MDS item I0020B. The Concept Analyzer also maps the entity to MDS item I2300, recommending the item is selected.

From "Patient presents with Anemia due to blood loss" the MCE identifies the entity "Anemia" as a disease. The Concept Analyzer maps this entity to an ICD10 code: "D64.9 (Anemia, unspecified)" and makes it available for consideration for MDS item I0020B. The Concept Analyzer will also map the entity to the MDS item I0200 recommending that the item be selected.

Document Annotator 218 takes the output of the previous components and marks up the original source material to provide the user interface with a resource to demonstrate to the user the context of the knowledge discovered, under an embodiment.

Case Analyzer

The analysis performed and actions taken by the Concept Analyzer (as described above) may be implemented within the Case Analyzer 220, under an embodiment. The Case Analyzer 220 is further described below.

Case Analyzer 220 is the component where the patient's disparate records are brought together for analysis. A patient may have multiple scanned documents (e.g. Health & Physical and discharge documents), documentation from the facility EMR (e.g. nursing notes, laboratory results, staff assessment results or BIMS results) and therapy documentation from the therapy EMR. The Case Analyzer may merge information from these sources, resolving conflicts, sorting conflicting information and adding derived conclusions.

The Case Analyzer employs rules based reasoning and deductive analysis to perform its function. The rules, for Case Analyzer, are crafted in two ways: interviews with clinical experts and from the operation of the Knowledge Learning System. The Knowledge learning system reviews selections made by the user community, in the tool, and contrasts with the input documentation knowledge. The Knowledge Learning System is looking for coding patterns in the set of data created by the users of the system.

The Case Analyzer transforms documentation knowledge to better match MDS rules. Examples of Case Analyzer rules follow.

If a patient has R62.7 (Adult Failure to Thrive) SUBSTITUTE E46 (Unspecified Protein-calorie malnutrition) AND ADD R63.8 (Other Symptoms and Signs concerning food & nutrition intake). In the settings for which this tools is aimed, Adult Failure to thrive is a result of the patient having inadequate food and nutritional intake. For the tool's target user community it is more appropriate to code E46 and R63.8 than R62.7 as it codes the cause rather than the consequence of the patient's issue.

An example of enriching documentation knowledge, to meet MDS coding guidelines, is as follows: IF patient had joint replacement surgery at the hospital ADD recommendation Z47.1 (Aftercare following joint replacement surgery). When a patient has joint replacement surgery the hospital will code the actual surgery and the skilled nursing facility will code for providing care to a patient recovering from joint replacement surgery. The hospital documentation will record the surgical event and the system needs to draw the conclusion that the post-surgical care is required as a consequence.

If the patient is being treated by a physical therapist (as identified in the EMR) who is administering a program of Therapeutic Exercise (as identified by the CPT code 97110) then add the recommended diagnosis M62.59—Muscle wasting and atrophy, not elsewhere classified, multiple sites. Therapeutic exercise provided under the supervision of a physical therapist is standard treatment for a patient with muscle wasting and atrophy issues.

If the Health and Physical documentation identifies the patient as obese and the nursing notes in the EMR documents leg ulcers the system will identify diabetes as a diagnosis to investigate. Obese patients with diabetes often develop leg ulcers due to circulation issues associated to their obesity and diabetes diagnoses.

If the patient has been prescribed albuterol-ipratropium the system will recommend the investigation of a possible diagnosis of J44.9—Chronic obstructive pulmonary disease, unspecified. Albuterol-ipratropium is a standard medication for addressing a diagnosis of Chronic pulmonary disease (COPD).

The Case Analyzer may detect conflicts among different EMR data sources. As discussed above, in a skilled nursing facility, two separate disciplines, nursing and speech therapy, may assess the patient's cognitive functions and record this information in two separate and unrelated EMR systems (i.e. a facility EMR and therapy EMR). The information recorded may be similar or very different as patient's interaction for cognitive function may differ based on the time of day, environment, hydration level, medication intake of the patient etc. In a perfect world, during a care plan meeting, the nurse and the speech language pathologist (SLP) would discuss their individual findings and then code the documentation based on which situation most accurately represents the individual patient. However, the different evaluations may persist in the two different EMR systems. The Case Analyzer identifies this conflict and may pass the information onto the user for resolution.

As these examples show the Case Analyzer helps the user uncover all the necessary details to accurately and completely code the patient in the medical record. The Case Analyzer may pass this coding information to the User Interface (FIG. 2B, 290) under an embodiment.

Electronic Medical Records System (EMR) Gateway

The EMR gateway interfaces with leading EMR systems used in skilled nursing facilities. In many facilities more than one EMR may be in use by different specialties, like nursing and therapy. The EMR gateway uses standard application programming interfaces (APIs) to extract relevant data on the patient case and to return MDS coding decisions.

Knowledge Learning System

Knowledge Learning Subsystem monitors choices and selections made by the end users of the system. It identifies patterns in system user choices for patients with certain characteristics, under an embodiment. As one example, coding diagnoses in ICD10 requires a certain level of specificity that is not always provided in the documentation. It is common for medical practitioners to abbreviate or under-specify common diagnoses with the expectation that the reader understands the intended code based on the clinical setting and the typical patient. The system user has this expertise to correctly choose the ICD10 code. This means that the system has the opportunity to discover the single code to recommend in these situations by reviewing the users selections. As indicated above, the Knowledge Learning System reviews selections made by the user community, in the tool, and contrasts with the input documentation knowledge. The Knowledge Learning System is looking for coding patterns in the set of data created by the users of the system. The Knowledge Learning System is an expert generated set of rules. The output of the Knowledge Learning System is fed back to the document analyzer and/or case analyzer expert systems via a workflow process that allows for a clinical appropriateness review.

User Interface (UI)

The User Interface (UI) 290 provides a method for the end user to engage with the discoveries of the medical knowledge mining system as implemented by the Document Analyzer and the Case Analyzer. The end user is provided the opportunity to review discoveries in the context of the source material. For example: a diagnosis recommendation derived from knowledge discovered in a scanned medical document will be presented to the user to show which language in the source document led to the recommendation. In this way the end user can see the source and the reasoning behind the conclusion and can express their agreement or disagreement. The actual decision made by the user may be recorded and used to train the document analyzer and case analyzer systems. The User Interface also provides a Coding Recommendations Review Wizard, a Selection Review Module, and a Reimbursement Calculator as further described below.

Coding Recommendations Review Wizard

Figure 7A:
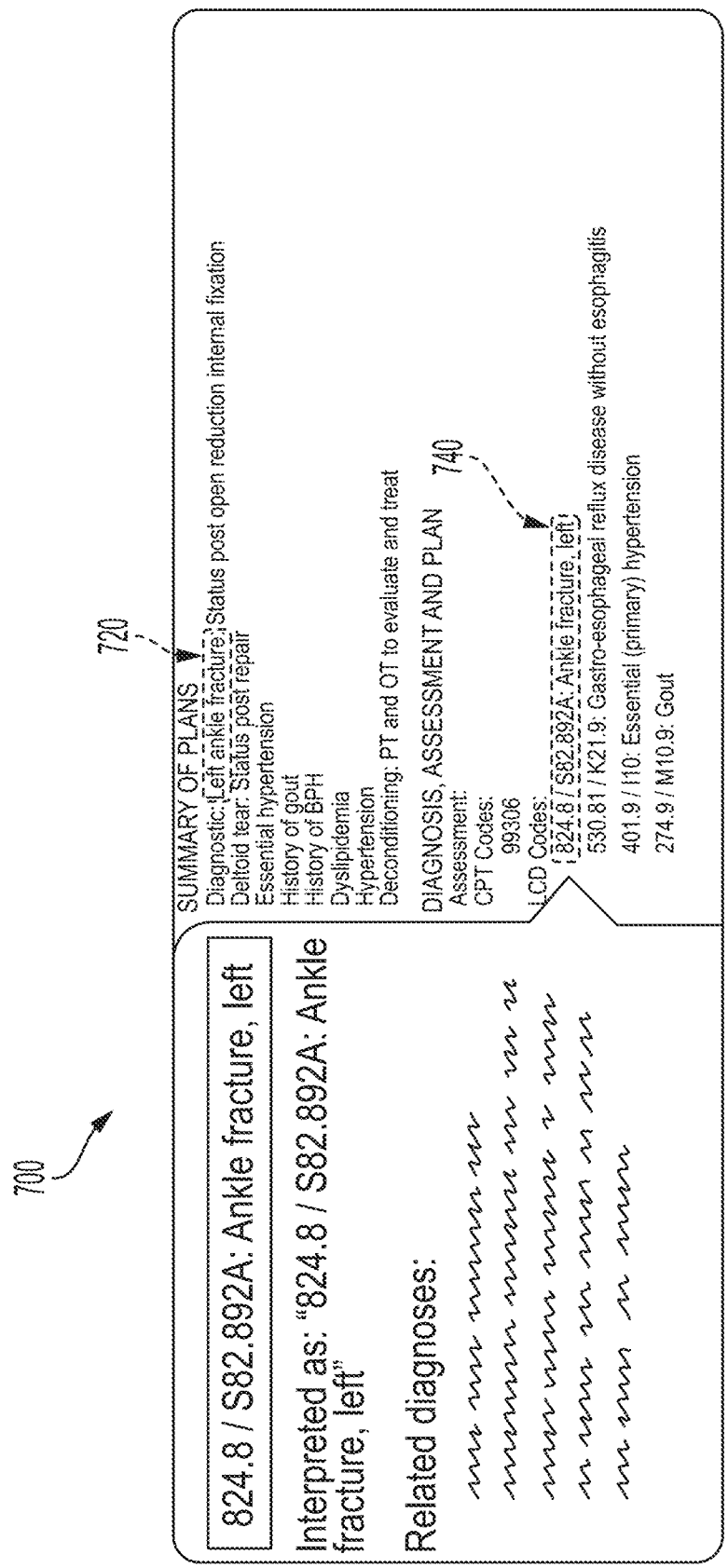
FIG. 7A shows an electronic data management user interface, under one embodiment.
Figure 7B:
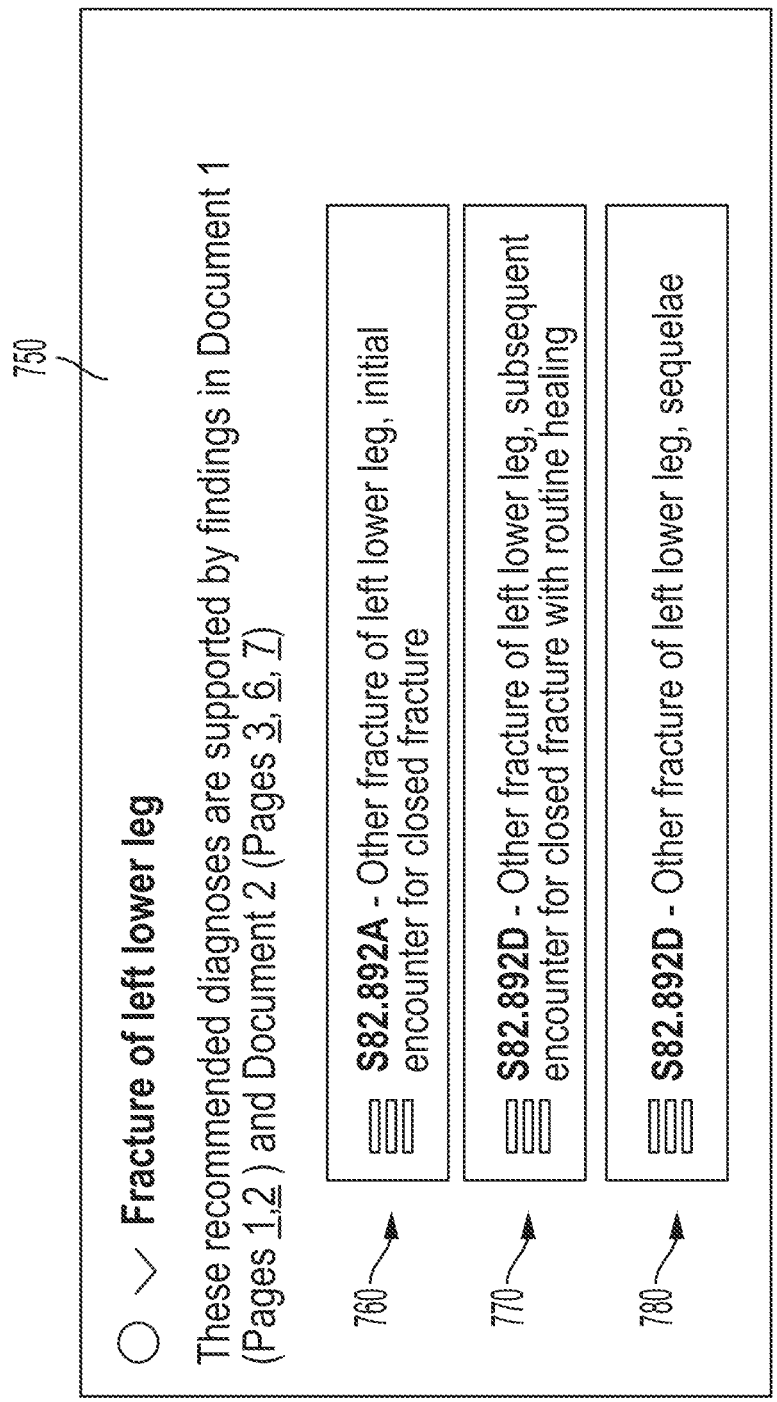
FIG. 7B shows an electronic data management user interface, under one embodiment.
Figure 8:
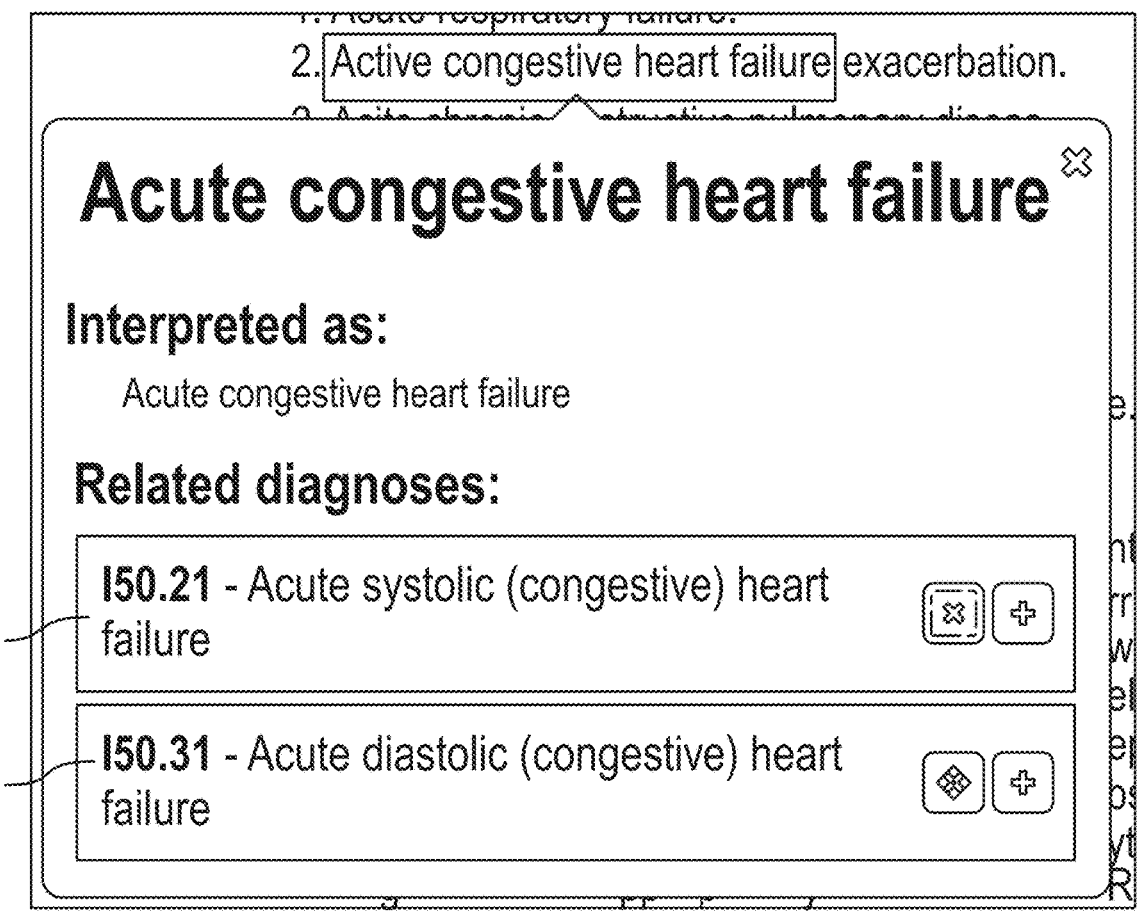
FIG. 8 shows an electronic data management user interface, under one embodiment.

The User Interface's primary function is to allow the User the opportunity to review the discoveries of the Case Analyzer and Document Analyzer. The Coding Recommendations Review Wizard (FIG. 2B, 250; FIGS. 7A, 7B, and 8)

is the set of screens constructed to simplify the process of reviewing the discoveries and knowledge from the backend.

Selection Review Module

The Selection Review Module (FIG. 2B, 260; FIG. 9) reviews the user's coding choices and reviews for potential conflicts, unusual combinations and possible improvements. It considers the users choices in concert with information discovered in the medical record by the document analyzer and case analyzer.

The Selections Review module reviews the user's choices to determine opportunities to highlight to the user information that would eliminate inconsistencies or identify potential mis-coded situations. The Selections Reviewer is constructed from a combination of rules system and recommender model. The rules system contains knowledge on MDS coding validations, common errors and coding patterns based on patient specifics. The recommender model is trained from a combination of data provided by coding experts and from the final selections of the users.

As one example of a common error, a user may have skipped sections of the MDS. The Selection Review Module may report this fact to a user. As an example of inconsistencies, a user may have coded a patient for coma and also have coded information relating to completed interviews. The Selection Review Module may report this inconsistency to a user.

Reimbursement Calculator

The Reimbursement Calculator (FIG. 2B, 270; FIG. 9) implements the reimbursement calculations. The output of the reimbursement Calculator is presented to the User through the set of screens supporting the Selection Review Module. The reimbursement amount is simply a consequence of the decisions made by the User in the Coding Recommendations Review Wizard.

FIGS. 3-8 show a workflow of the PDPM in operation at a skilled nursing facility, under an embodiment.

Figure 3:
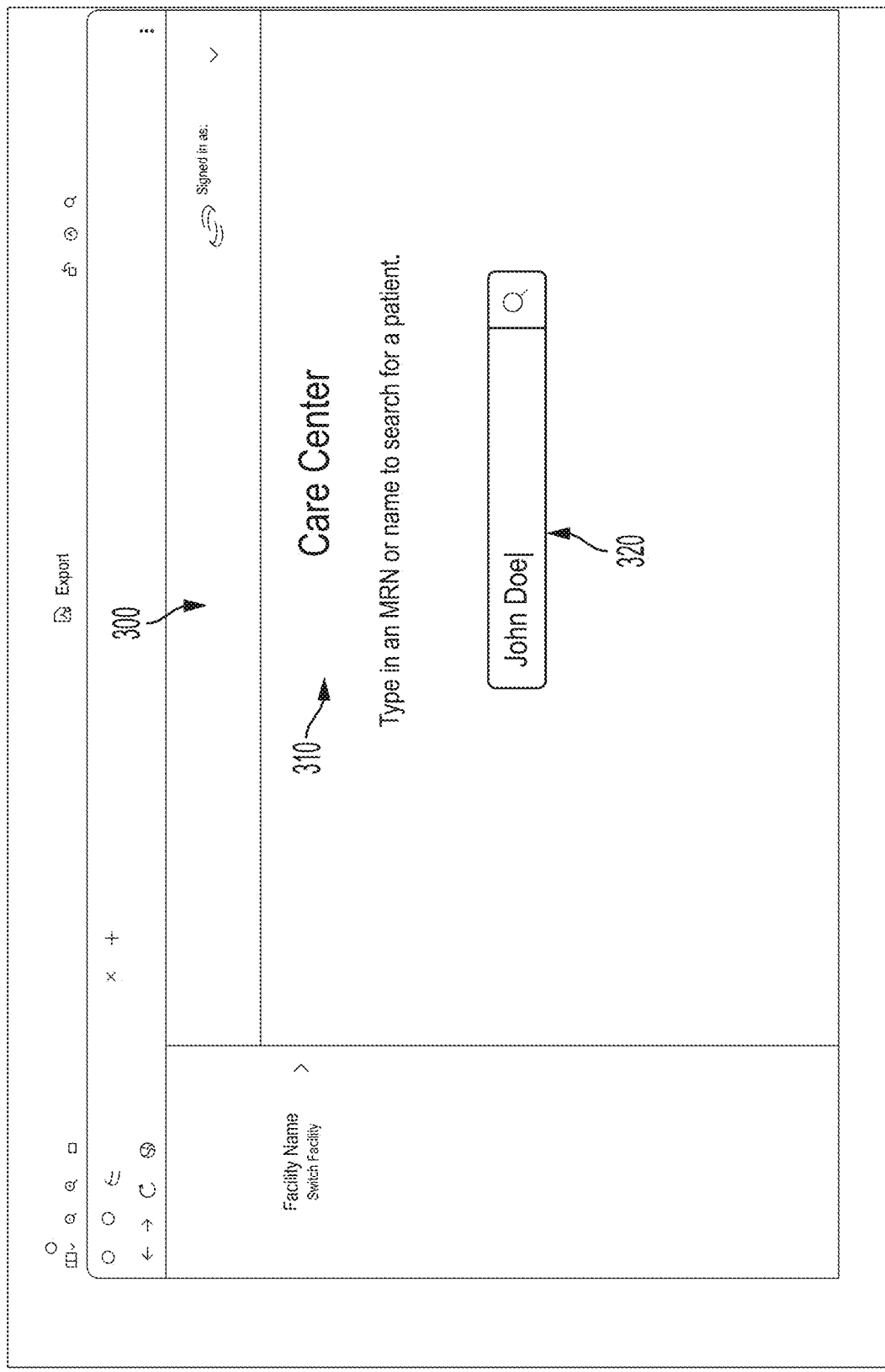
FIG. 3 shows an electronic data management user interface, under an embodiment.

FIG. 3 shows an interface 300 allowing a user at facility 310 to query 320 patient name or Medical Record Number (MRN).

Figure 4:
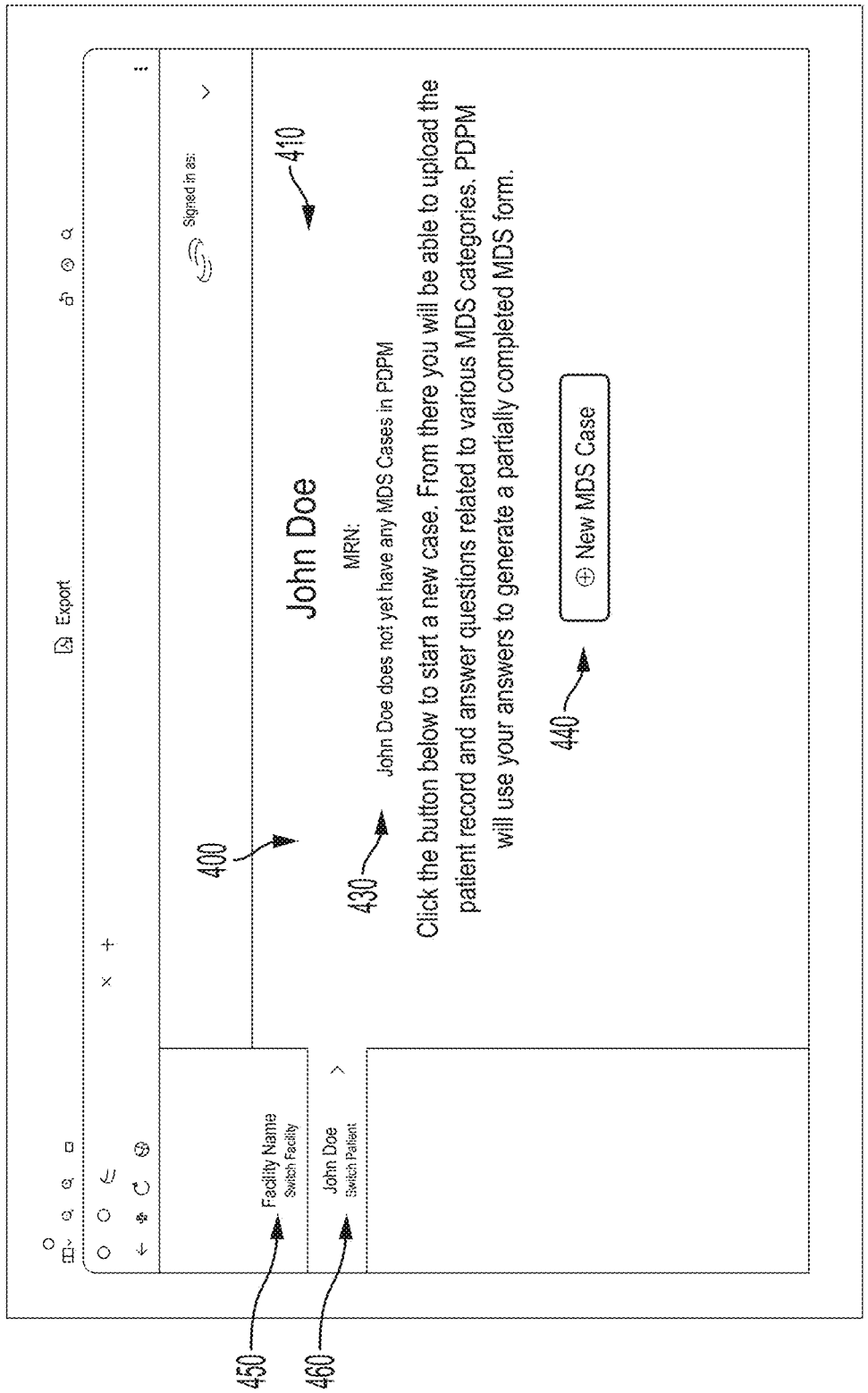
FIG. 4 shows an electronic data management user interface, under an embodiment.

FIG. 4 provides a patient screen 400 showing name and Medical Record Number (MRN) of John Doe 410. The screen indicates 420 that "John Doe does not yet have any MDS Cases in PDPM." FIG. 4 then states 430: "Click the button below to start a new case. From there you will be able to upload the patient record and answer questions related to various MDS categories. PDPM will use your answers to generate a partially completed MDS form." The screen and workflow screens in general display care center 450 and patient name 460 in the upper left screen. The screen provides a clickable option 440 to advance workflow to MDS entry for the indicated patient.

FIG. 5 illustrates a workflow screen 500 requesting MDS coding decisions from the user. The screen 500 specifically requests information regarding section M0300 B1 of the MDS entitled "Unhealed Stage 2 Pressure Ulcers" 510. The left side of the screen shows user progress through sections 550 of the MDS. FIG. 5 shows that the user is completing Section M (552). The screen 500 provides interface options 520 for inputting coding decisions and provides resources 530 to assist coding decisions. The resources 530 correspond to Resident Assessment Instrument resources for those assessing the needs and conditions of residents in long term care settings. The Resident Assessment Instrument/Minimum Data Set (RAI/MDS) is a comprehensive assessment and care planning process used by the nursing home industry as a requirement for nursing home participation in the Medicare and Medicaid programs. Note that PDPM does not present annotated documentation as part of this screen as PDPM did not identify any underlying documentation relating to this section of the MDS. However, the PDPM is capable of presenting documentation relating to this section when identified.

Figure 6:
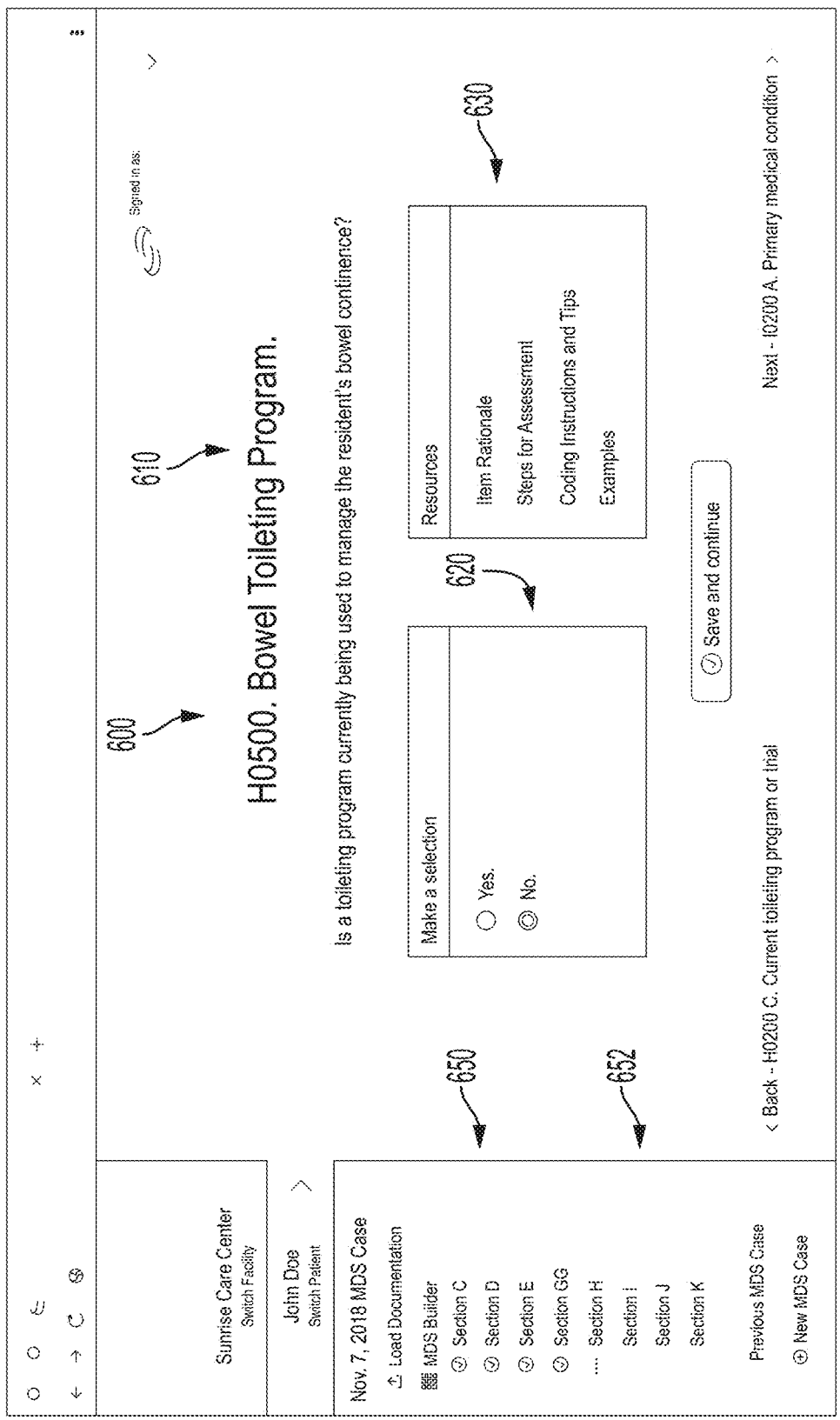
FIG. 6 shows an electronic data management user interface, under one embodiment.

FIG. 6 illustrates a workflow screen 600 requesting MDS coding decisions from the user. The screen 600 specifically requests information regarding section H0500 of the MDS entitled "Bowel Toileting Program" 610. The left side of the screen shows user progress through sections 650 of the MDS. FIG. 6 shows that the user is completing Section H (652). The screen 600 provides interface options 620 for inputting coding decisions and provides resources 630 to assist coding decisions. The resources 630 correspond to Resident Assessment Instrument resources for those assessing the needs and conditions of residents in long term care settings. Note that PDPM does not present annotated documentation as part of this screen as PDPM did not identify any underlying documentation relating to this section of the MDS. However, the PDPM is capable of presenting documentation relating to this section when identified.

FIGS. 7A and 7B provide a screenshot demonstrating the Coding Recommendation and Review Wizard 260 described above.

FIG. 7A shows specific output of the Document Annotator. The screen of FIG. 7A shows sections of underlying unstructured data 700 received from a health and physical report. The Document Annotator displays a "Summary of Plans" section. This section 710 provides the following diagnostic: "Left ankle fracture" 720. The Document Annotator also shows a "Diagnosis, Assessment, and Plan" section. This section shows an ICD code specifically for ankle fracture, left 740. The presence of specific ICD 10 codes in the "Diagnosis, Assessment, and Plan" section allows the Concept Analyzer and/or Case Analyzer to confirm ICD 10 codes relating to left ankle fracture directly as already described above. The Concept Analyzer and/or Case Analyzer then maps the ICD 10 coding to MDS coding recommendations. The Coding Recommendations Review Wizard provides MDS coding recommendations. As seen in FIG. 7B the Coding Recommendations Review Wizard 750 provides coding options for patient conditions at the SNF. The coding options include S82.892A—Other fracture of left lower leg, initial encounter for closed fracture (760), S82.892D—Other fracture of left lower leg, subsequent encounter for closed fracture with routine healing (770), and S82.892S—Other fracture of left lower leg, sequelae (780). For example, the user of the PDPM system reviews the coding recommendations and may select an option as appropriate. Note that the system recognizes from the information shown in FIG. 7A that the hospital (or discharge facility) coded the fracture as an initial encounter. Based on this information, the system (as seen in FIG. 7B) provides the user an option to code the SNF's encounter with the patient as a subsequent encounter.

FIG. 8 demonstrates the Coding Recommendation and Review Wizard 260 described above. The image demonstrates a situation where the documentation has not provided sufficient information to completely identify a single ICD10 code. The end user is being requested to investigate other documentation sources, not already provided to the system, to make the final determination as to the correct coding. In this example, the documentation has identified the patient has having "acute congestive heart failure" but correct coding requires a higher level of specificity. The end user will need to choose between 150.21—Acute Systolic (congestive) Heart Failure (810) or 150.31—Acute Diastolic (congestive) Heart Failure (820).

FIG. 9A and FIG. 9B shows an MDS case review screen. In particular, the interface of FIG. 9A and FIG. 9B provides automated recommendations for MDS items based on information found in facility EMRs as well as uploaded documents. Under an embodiment, a single recommendation might increase the estimated Medicare reimbursement. In other cases, a combination of accepted recommendations may have a significant impact on reimbursement. The interface of FIG. 9A shows that 3 recommendations have been identified as an instance of significant reimbursement impact if all 3 are accepted. Note the user may have adopted system recommendations prior to reaching the review screen of FIG. 9. The recommendations shown on the review page represent MDS coding recommendations that the user may have previously rejected, under an embodiment. The user is asked to review each MDS item to see the details of the recommendation. The user may then accept any combination of the recommendations. FIG. 9A shows recommended diagnosis and actions 912 and recommended values 914. The user has an option to accept a previously declined diagnosis of Metabolic Encephalopathy. The user has an option to accept a previously declined diagnosis of Pneumonia/Dysphagia. The user has an option to accept a previously declined recommendation of a Mechanically Altered Diet. If all 3 recommendations are accepted, the estimated reimbursement and case-mix indices/groups for listed rate components change as seen in section 920 of FIG. 9. The review page of FIG. 9 shows the increased reimbursement if all recommendations are accepted.

Note that reimbursement information may be provided to users at different points in the PDPM workflow. For example, prior to reaching the review screen of FIGS. 9A and 9B, reimbursement information may be provided to the user corresponding to coding recommendations adopted by the user. This reimbursement information comprises the reimbursement resulting from end user decisions to adopt PDPM coding recommendations.

A method is described herein comprising under an embodiment receiving scanned documents, wherein the scanned documents comprise unstructured data. The method includes performing optical character recognition of the scanned documents to produce text data for each page of the scanned documents, wherein the text data for each page comprises a sequence of words stored together with their location as x, y coordinates. The method includes dividing each page of the scanned documents into subsections. The method includes using the text data to identify a structure type of each subsection of a page, wherein the structure type includes at least one of a table and text paragraph. The method includes using the text data to label each subsection of a page with a semantic type, wherein the semantic type defines a context surrounding collection of information in a subsection. The method includes using the text data for each subsection of a page to identify medical concepts.

The dividing each page into subsections comprises applying a page blocker, wherein the page blocker identifies vectors of pixel density in the vertical and horizontal direction to identify vertical and horizontal page breaks, under an embodiment.

The dividing each page into subsections includes summing the foreground color along the vertical and horizontal vectors of pixel density, under an embodiment.

The dividing each page into subsections includes reviewing each vertical pixel density vector to identify an occurrence of a vertical section break, wherein the occurrence of a vertical section break comprises the summed foreground color value for a vertical pixel density vector falling below a threshold value, under an embodiment.

The dividing each page into subsections includes reviewing each horizontal pixel density vector to identify an occurrence of a horizontal section break, wherein the occurrence of a horizontal section break comprises the summed foreground color value for a horizontal pixel density vector falling below a threshold value, under an embodiment.

The identifying a structure type includes applying a structure classifier, wherein the structure classifier comprises a multi-stage neural network that assigns a probability of structure type to each subsection of a page, under an embodiment.

The multi-stage neural network of an embodiment comprises a first independent neural network comprising 4 2-dimension convolutional layers with 65 filters and max pooling.

A 100×100 matrix of vertical and horizontal pixel density values of a subsection is fed into the first independent neural network, under an embodiment.

The multi-stage neural network of an embodiment comprises a second independent neural network comprising 3 1-dimension convolutional layers with a single filter and max pooling.

A 100 element vector of horizontal pixel density values of a subsection is fed into the second independent neural network, under an embodiment.

The multi-stage neural network of an embodiment comprises a third independent neural network comprising 3 1-dimension convolutional layers with a single filter and max pooling.

A 100 element vector of vertical pixel density values is fed into the third independent neural network, under an embodiment.

Results of the first neural network, the second neural network, and the third neural network are combined and fed into a fourth fully connected 3 layer neural network for classification of a subsection, under an embodiment.

The labelling of each subsection with a semantic type comprises applying a text classifier to each subsection of a page, wherein the text classifier comprises an unsupervised learning algorithm for obtaining vector representations of words in each subsection, under an embodiment.

The unsupervised learning algorithm of an embodiment comprises a Global Vectors for Word Representation model trained on samples of text from hospital documentation.

The semantic type label includes at least one of medications, physical exam, lab results, radiology results, therapy notes, nursing notes, patient information, hospital boilerplate, and patient education, under an embodiment.

Upon an occurrence of the structure classifier assessing a subsection of a page with high probability of being a table, the page blocker tests a potential split of the subsection into subdivisions using the structure classifier and the text classifier, under an embodiment.

The testing comprises assigning a semantic unity score to each subdivision, wherein the semantic unity score indicates a probability that each subdivision is correctly labelled by the text classifier, wherein the semantic unity score is computed using a Gini Impurity method, under an embodiment.

The method of an embodiment includes maintaining the potential subdivision upon the successful occurrence of a first event, wherein the first event includes the structure type probability of being a table for at least one of the subdivisions improving and the semantic unity score of both subdivisions improving.

The identifying the medical concepts comprises applying a medical concept extractor to the text data for each subsection of a page, wherein the medical concept extractor comprises a language model built using an open source ScispaCy model, wherein the model is trained on biomedical documents, under an embodiment.

The method of an embodiment translates the medical concepts and information of at least one of the structure type and semantic type into entries for a Minimum Data Set, wherein the Minimum data set comprises a set of data elements for mandatory collection and reporting assessments relating to all residents in Medicare and Medicaid certified nursing homes.

Computer networks suitable for use with the embodiments described herein include local area networks (LAN), wide area networks (WAN), Internet, or other connection services and network variations such as the world wide web, the public internet, a private internet, a private computer network, a public network, a mobile network, a cellular network, a value-added network, and the like. Computing devices coupled or connected to the network may be any microprocessor controlled device that permits access to the network, including terminal devices, such as personal computers, workstations, servers, mini computers, main-frame computers, laptop computers, mobile computers, palm top computers, hand held computers, mobile phones, TV set-top boxes, or combinations thereof. The computer network may include one of more LANs, WANs, Internets, and computers. The computers may serve as servers, clients, or a combination thereof.

The systems and methods for extracting patient diagnostics from disparate documentation can be a component of a single system, multiple systems, and/or geographically separate systems. The systems and methods for extracting patient diagnostics from disparate documentation can also be a subcomponent or subsystem of a single system, multiple systems, and/or geographically separate systems. The components of the systems and methods for extracting patient diagnostics from disparate documentation can be coupled to one or more other components (not shown) of a host system or a system coupled to the host system.

One or more components of the systems and methods for extracting patient diagnostics from disparate documentation and/or a corresponding interface, system or application to which the systems and methods for extracting patient diagnostics from disparate documentation is coupled or connected includes and/or runs under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components, and/or provided by some combination of algorithms. The methods described herein can be implemented in one or more of software algorithm(s), programs, firmware, hardware, components, circuitry, in any combination.

The components of any system that include the systems and methods for extracting patient diagnostics from disparate documentation can be located together or in separate locations. Communication paths couple the components and include any medium for communicating or transferring files among the components. The communication paths include wireless connections, wired connections, and hybrid wireless/wired connections. The communication paths also include couplings or connections to networks including local area networks (LANs), metropolitan area networks (MANs), wide area networks (WANs), proprietary networks, interoffice or backend networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Aspects of the systems and methods for extracting patient diagnostics from disparate documentation and corresponding systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the systems and methods for extracting patient diagnostics from disparate documentation and corresponding systems and methods include: microcontrollers with memory (such as electronically erasable programmable read only memory (EEPROM)), embedded microprocessors, firmware, software, etc. Furthermore, aspects of the systems and methods for extracting patient diagnostics from disparate documentation and corresponding systems and methods may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that any system, method, and/or other components disclosed herein may be described using computer aided design tools and expressed (or represented), as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described components may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the systems and methods for extracting patient diagnostics from disparate documentation is not intended to be exhaustive or to limit the systems and methods to the precise forms disclosed. While specific embodiments of, and examples for, the systems and methods for extracting patient diagnostics from disparate documentation and corresponding systems and methods are described herein for illustrative purposes, various equivalent modifications are possible within the scope of the systems and methods, as those skilled in the relevant art will recognize. The teachings of the systems and methods for extracting patient diagnostics from disparate documentation and corresponding systems and methods provided herein can be applied to other systems and methods, not only for the systems and methods described above.

The elements and acts of the various embodiments described above can be combined to provide further embodiments. These and other changes can be made to the systems and methods for extracting patient diagnostics from disparate documentation and corresponding systems and methods in light of the above detailed description.

We claim:

1. A method comprising,
receiving scanned documents, wherein the scanned documents comprise unstructured data;
performing optical character recognition of the scanned documents to produce text data for each page of the scanned documents, wherein the text data for each page comprises a sequence of words stored together with their location as x, y coordinates;
dividing each page of the scanned documents into subsections, wherein the dividing each page into subsections comprises applying a page blocker, wherein the page blocker identifies vectors of pixel density in the vertical and horizontal direction to identify vertical and horizontal page breaks;
using the text data to identify a structure type of each subsection of a page, wherein the structure type includes at least one of a table and text paragraph, wherein the identifying a structure type includes applying a structure classifier, wherein the structure classifier comprises a multi-stage neural network that assigns a probability of structure type to each subsection of a page;
using the text data to label each subsection of a page with a semantic type, wherein the semantic type defines a context surrounding collection of information in a subsection; and
using the text data for each subsection of a page to identify medical concepts.

2. The method of claim 1, wherein the dividing each page into subsections includes summing the foreground color along the vertical and horizontal vectors of pixel density.

3. The method of claim 2, wherein the dividing each page into subsections includes reviewing each vertical pixel density vector to identify an occurrence of a vertical section break, wherein the occurrence of a vertical section break comprises the summed foreground color value for a vertical pixel density vector falling below a threshold value.

4. The method of claim 3, wherein the dividing each page into subsections includes reviewing each horizontal pixel density vector to identify an occurrence of a horizontal section break, wherein the occurrence of a horizontal section break comprises the summed foreground color value for a horizontal pixel density vector falling below a threshold value.

5. The method of claim 1, wherein the multi-stage neural network comprises a first independent neural network comprising four (4) 2-dimension convolutional layers with 65 filters and max pooling.

6. The method of claim 5, wherein a 100×100 matrix of vertical and horizontal pixel density values of a subsection is fed into the first independent neural network.

7. The method of claim 6, wherein the multi-stage neural network comprises a second independent neural network comprising three (3) 1-dimension convolutional layers with a single filter and max pooling.

8. The method of claim 7, wherein a 100 element vector of horizontal pixel density values of a subsection is fed into the second independent neural network.

9. The method of claim 8, wherein the multi-stage neural network comprises a third independent neural network comprising three (3) 1-dimension convolutional layers with a single filter and max pooling.

10. The method of claim 9, wherein a 100 element vector of vertical pixel density values is fed into the third independent neural network.

11. The method of claim 10, wherein results of the first neural network, the second neural network, and the third neural network are combined and fed into a fourth fully connected 3 layer neural network for classification of a subsection.

12. The method of claim 1, wherein the labelling of each subsection with a semantic type comprises applying a text classifier to each subsection of a page, wherein the text classifier comprises an unsupervised learning algorithm for obtaining vector representations of words in each subsection.

13. The method of claim 12, wherein the unsupervised learning algorithm comprises a Global Vectors for Word Representation model trained on samples of text from hospital documentation.

14. The method of claim 13, wherein the semantic type label includes at least one of medications, physical exam, lab results, radiology results, therapy notes, nursing notes, patient information, hospital boilerplate, and patient education.

15. The method of claim 14, wherein upon an occurrence of the structure classifier assessing a subsection of a page with high probability of being a table, the page blocker tests a potential split of the subsection into subdivisions using the structure classifier and the text classifier.

16. The method of claim 15, wherein the testing comprises assigning a semantic unity score to each subdivision, wherein the semantic unity score indicates a probability that each subdivision is correctly labelled by the text classifier, wherein the semantic unity score is computed using a Gini Impurity method.

17. The method of claim 16, maintaining the potential subdivision upon the successful occurrence of a first event, wherein the first event includes the structure type probability of being a table for at least one of the subdivisions improving and the semantic unity score of both subdivisions improving.

18. The method of claim 1, wherein the identifying the medical concepts comprises applying a medical concept extractor to the text data for each subsection of a page, wherein the medical concept extractor comprises a language model built using an open source ScispaCy model, wherein the model is trained on biomedical documents.

19. The method of claim 18, translating the medical concepts and information of at least one of the structure type and semantic type into entries for a Minimum Data Set, wherein the Minimum data set comprises a set of data elements for mandatory collection and reporting assessments relating to all residents in Medicare and Medicaid certified nursing homes.

* * * * *